United States Patent
Yamagishi

(10) Patent No.: US 10,597,725 B2
(45) Date of Patent: Mar. 24, 2020

(54) PRIMER REAGENT FOR AMPLIFYING ALK FUSION GENE, ALK FUSION GENE AMPLIFICATION REAGENT KIT INCLUDING THE SAME, AND ALK FUSION GENE AMPLIFICATION METHOD AND ALK FUSION GENE ANALYSIS METHOD USING THE SAME

(71) Applicant: ARKRAY, Inc., Kyoto (JP)

(72) Inventor: Marifu Yamagishi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 939 days.

(21) Appl. No.: 14/841,818

(22) Filed: Sep. 1, 2015

(65) Prior Publication Data

US 2016/0097103 A1    Apr. 7, 2016

(30) Foreign Application Priority Data

Sep. 1, 2014 (JP) .................................. 2014-177356
Aug. 24, 2015 (JP) .................................. 2015-165306

(51) Int. Cl.
C12Q 1/68     (2018.01)
C12Q 1/6886   (2018.01)

(52) U.S. Cl.
CPC ..... *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 7,250,496 B2* | 7/2007 | Bentwich | ............... | G06F 19/18 435/320.1 |
| 7,605,131 B2* | 10/2009 | Mano | ..................... | C07K 14/47 514/1.1 |
| 7,728,120 B2* | 6/2010 | Mano | ..................... | C07K 14/47 536/23.4 |
| 7,964,710 B2* | 6/2011 | Mano | ..................... | C07K 14/47 536/23.4 |
| 9,175,350 B2* | 11/2015 | Sanders | ............... | C12Q 1/6886 |
| 9,428,812 B2* | 8/2016 | Hout | .................... | C12Q 1/6886 |
| 2009/0099193 A1 | 4/2009 | Mano et al. | | |
| 2009/0156475 A1 | 6/2009 | Rikova et al. | | |
| 2012/0282609 A1 | 11/2012 | Hirai et al. | | |

FOREIGN PATENT DOCUMENTS

| | | |
|---|---|---|
| JP | 4303303 B2 | 5/2009 |
| JP | 2010-501175 A | 1/2010 |
| JP | 2012-100628 A | 5/2012 |
| JP | 2013-081448 A | 5/2013 |
| WO | 20111087709 A2 | 7/2011 |

OTHER PUBLICATIONS

Lowe et al. (Nucleic Acids Research, 1990, 18(7):1757-1761) (Year: 1990).*

(Continued)

*Primary Examiner* — Stephanie K Mummert
(74) *Attorney, Agent, or Firm* — Morgan, Lewis & Bockius LLP

(57) ABSTRACT

The present disclosure provides a novel primer reagent for detecting a plurality of variants of the ALK fusion gene.

12 Claims, 4 Drawing Sheets

Specification includes a Sequence Listing.

(56) References Cited

OTHER PUBLICATIONS

Zinnin et al. (2014, Biol. Direct 9 (1), 20) (Year: 2014).*
Koivunen, J.P., et al., "EML4-ALK fusion gene and efficacy of an ALK kinase inhibitor in lung cancer", Clin Cancer Res 2008; 14(13) 4275-83.
Wong DW, et al., "The EML4-ALK Fusion Gene Is Involved in Various Histologic Types of LungCancers From Nonsmokers With Wild-type EGFR and KRAS", Cancer 2009; 115: 1723-33.
Wong DW, et al., "A Novel KIF5B-ALK Variant in Nonsmall Cell Lung Cancer", Cancer 2011; 117:2709-2718.
Soda, M., et al., "Identification of the transforming EML4-ALK fusion gene in non-small-cell lungcancer", Nature 2007; 448: 561-566.
Extended European Search Report issued in corresponding European Patent Application No. 15183368.8 dated Jan. 22, 2016.
Sanders et al., "*Homo sapiens* EML4-ALK fusion protein variant 8a mRNA partial cds," Database accession No. GU797894.1, Database GenBank [Online] NCBI, (2011).
Sanders et al., "*Homo sapiens* EML4-ALK fusion protein variant 8b mRNA partial cds," Database accession No. GU797895.1, Database GenBank [Online] NCBI, (2011).
Soda et al., "*Homo sapiens* EML4-ALK mRNA for EML4-ALK fusion protein, complete cds," Database accession No. AB663645.1, Database GenBank [Online] NCBI, (2012).
Togashi et al., "*Homo sapiens* KLC1-ALK mRNA for KLC1-ALK fusion protein, partial cds," Database accession No. AB781674.1, Database GenBank [Online] NCBI, (2013).
Soda et al., "*Homo sapiens* mRNA for fusion protein EML4-ALK variant 1, complete cds," Database accession No. AB274722.1, Database GenBank [Online] NCBI, (2008).
Soda et al., "*Homo sapiens* mRNA for fusion protein EML4-ALK variant 2, complete cds," Database accession No. AB275889.1, Database GenBank [Online] NCBI, (2008).
Choi et al., "*Homo sapiens* mRNA for fusion protein EML4-ALK variant 3 splicing isoform a, complete cds," Database accession No. AB374361.1, Database GenBank [Online] NCBI, (2008).
Choi et al., "*Homo sapiens* mRNA for fusion protein EML4-ALK variant 3 splicing isoform b, complete cds," Database accession No. AB374362.1, Database GenBank [Online] NCBI, (2008).
Takeuchi et al., "*Homo sapiens* mRNA for fusion protein EML4-ALK variant 4, complete cds," Database accession No. AB374363.1, Database GenBank [Online] NCBI, (2008).
Takeuchi et al., "*Homo sapiens* mRNA for fusion protein EML4-ALK variant 5 splicing isoformi a, complete cds," Database accession No. AB374364.1, Database GenBank [Online] NCBI, (2009).
Takeuchi et al., "*Homo sapiens* mRNA for fusion protein EML4-ALK variant 5 splicing isoformi b, complete cds," Database accession No. AB374365.1, Database GenBank [Online] NCBI, (2008).
Takeuchi et al., "*Homo sapiens* EML4-ALK variant 6 mRNA for fusion protein EML4-ALK variant 6, complete cds," Database accession No. AB462411.1, Database GenBank [Online] NCBI, (2015).
Takeuchi et al., "*Homo sapiens* EML4-ALK variant 7 mRNA for fusion protein EML4-ALK variant 7, complete cds," Database accession No. AB462412.1, Database GenBank [Online] NCBI, (2015).
Office Action issued in corresponding European Patent Application No. 15183368.8 dated Sep. 30, 2016.
Office Action issued in corresponding Japanese Patent Application No. 2015-165306 dated Nov. 13, 2018.
Sanders et al., "Exon scanning by reverse transcriptase-polymerase chain reaction for detection of known and novel EML4-ALK fusion variants in non-small cell lung cancer," Cancer Genetics, 204: 45-52 (2011).
Koivunen et al., "EML4-ALK Fusion Gene and Efficacy of an ALK Kinase Inhibitor in Lung Cancer," Clinical Cancer Research, 14: 4275-4283 (2008).
Wong et al., "The EML4-ALK Fusion Gene Is Involved in Various Histologic Types of Lung Cancers from Nonsmokers With Wild-type EGFR and KRAS," Cancer, 1723-1733 (2009).
Takeuchi et al., "KIF5B-ALK, a Novel Fusion Oncokinase Identified by an Immunohistochemistry-based Diagnostic System for ALK-positive Lung Cancer," Clinical Cancer Research, 15: 3143-3149 (2009).
Shinmura et al., "EML4-ALK fusion transcripts in immunohistochemically ALK-positive non-small cell lung carcinomas," Experimental and Therapeutic Medicine, 1: 271-275 (2010).
Wong et al., "A Novel KIF5B-ALK Variant in Nonsmall Cell Lung Cancer," Cancer, 2709-2718 (2011).
Togashi et al., "KLC1-ALK: A Novel Fusion in Lung Cancer Identified Using a Formalin-Fixed Paraffin-Embedded Tissue Only," PLOS One, 7: e31323 (2012).

* cited by examiner

SEQUENCE LISTING

<160> NUMBER OF SEQ ID NOS: 49

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
cctgggaaag gacctaaag                                            19

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
gggagactat gaaatattgt acttg                                     25

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
ataaagatgt catcatcaac caag                                      24

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
gcgaaaaaaa cagccaag                                             18

<210> SEQ ID NO 5
<211> LENGTH: 16
<212> TYPE: DNA
<213> ORGANISM: Artificial Sequence

```
<220> FEATURE:
<223> OTHER INFORMATION: primer

<400> SEQUENCE: 5
gctccatctg catggc                                                     16

<210> SEQ ID NO 6
<211> LENGTH: 14
<212> TYPE: DNA
<213> ORGANISM: Artificial Sequence
<220> FEATURE:
<223> OTHER INFORMATION: primer

<400> SEQUENCE: 6
tggcagcctg gccc                                                       14

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
ataggaacgc actcaggc                                                   18

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
aaatgtggaa tgctgccag                                                  19

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
gagatatgct ggatgagcc                                                  19

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
gaaggaaagg cagatcaatt tttag                                           25

<210> SEQ ID NO 11
<211> LENGTH: 17
<212> TYPE: DNA
<213> ORGANISM: Artificial Sequence
<220> FEATURE:
<223> OTHER INFORMATION: primer

<400> SEQUENCE: 11
tacactgcag gtgggtg                                                    17
```

```
<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
tgtagtcggt catgatgg                                                 18

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
gtgaaaaaat cagtctcaag taaag                                         25

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
gatctgaats ctgaaagaga aatag                                         25

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tgtgatgcgc tactcaatag                                               20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cctggatctc catatcctcc                                               20

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
ggcattctgc acagattg                                                 18

<210> SEQ ID NO 18
<211> LENGTH: 21
<212> TYPE: DNA
<213> ORGANISM: Artificial Sequence
<220> FEATURE:
<223> OTHER INFORMATION: primer
```

```
<400> SEQUENCE: 18
agaaatagga attgctgtgg g                                          21

<210> SEQ ID NO 19
<211> LENGTH: 17
<212> TYPE: DNA
<213> ORGANISM: Artificial Sequence
<220> FEATURE:
<223> OTHER INFORMATION: primer

<400> SEQUENCE: 19
ccagcttcga gcacaag                                               17

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
gggagtttgg ttctgtagat g                                          21

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
ttccaccaat attcctgaaa atg                                        23

<210> SEQ ID NO 22
<211> LENGTH: 14
<212> TYPE: DNA
<213> ORGANISM: Artificial Sequence
<220> FEATURE:
<223> OTHER INFORMATION: probe

<400> SEQUENCE: 22
caccaggagc tgca                                                  14

<210> SEQ ID NO 23
<211> LENGTH: 17
<212> TYPE: DNA
<213> ORGANISM: Artificial Sequence
<220> FEATURE:
<223> OTHER INFORMATION: probe

<400> SEQUENCE: 23
cctgtgtagt gcttcaa                                               17

<210> SEQ ID NO 24
<211> LENGTH: 13
<212> TYPE: DNA
<213> ORGANISM: Artificial Sequence
<220> FEATURE:
<223> OTHER INFORMATION: probe

<400> SEQUENCE: 24
agctccgcac ctc                                                   13

<210> SEQ ID NO 25
```

```
<211> LENGTH: 15
<212> TYPE: DNA
<213> ORGANISM: Artificial Sequence
<220> FEATURE:
<223> OTHER INFORMATION: probe

<400> SEQUENCE: 25
ccatgttgca gctga                                                      15

<210> SEQ ID NO 26
<211> LENGTH: 14
<212> TYPE: DNA
<213> ORGANISM: Artificial Sequence
<220> FEATURE:
<223> OTHER INFORMATION: probe

<400> SEQUENCE: 26
caccaggagc tgca                                                       14

<210> SEQ ID NO 27
<211> LENGTH: 18
<212> TYPE: DNA
<213> ORGANISM: Artificial Sequence
<220> FEATURE:
<223> OTHER INFORMATION: probe

<400> SEQUENCE: 27
agtaaaggtt cagagctc                                                   18

<210> SEQ ID NO 28
<211> LENGTH: 14
<212> TYPE: DNA
<213> ORGANISM: Artificial Sequence
<220> FEATURE:
<223> OTHER INFORMATION: probe

<400> SEQUENCE: 28
caccaggagc tgca                                                       14

<210> SEQ ID NO 29
<211> LENGTH: 18
<212> TYPE: DNA
<213> ORGANISM: Artificial Sequence
<220> FEATURE:
<223> OTHER INFORMATION: primer

<400> SEQUENCE: 29
aacagcctgc caccttac                                                   18

<210> SEQ ID NO 30
<211> LENGTH: 18
<212> TYPE: DNA
<213> ORGANISM: Artificial Sequence
<220> FEATURE:
<223> OTHER INFORMATION: primer

<400> SEQUENCE: 30
agtcatggca ccctgagg                                                   18

<210> SEQ ID NO 31
<211> LENGTH: 14
<212> TYPE: DNA
<213> ORGANISM: Artificial Sequence
<220> FEATURE:
<223> OTHER INFORMATION: probe

<400> SEQUENCE: 31
```

```
ctcagggctt ggcc                                                      14
```

<210> SEQ ID NO 32
<211> LENGTH: 540
<212> TYPE: DNA
<213> ORGANISM: Artificial Sequence
<220> FEATURE:
<223> OTHER INFORMATION: oligonucleotide

<400> SEQUENCE: 32

```
gggaaatatg aaaagccaaa atttgtgcag tgtttagcat tcttggggaa tggagatgtt    60
cttactggag actcaggtgg agtcatgctt atatggagca aaactactgt agagcccaca   120
cctgggaaag gacctaaagt gtaccgccgg aagcaccagg agctgcaagc catgcagatg   180
gagctgcaga gccctgagta caagctgagc aagctccgca cctcgaccat catgaccgac   240
tacaaccccca actactgctt tgctggcaag acctcctcca tcagtgacct gaaggaggtg   300
ccgcggaaaa acatcaccct cattcggggt ctgggccatg gagcctttgg ggaggtgtat   360
gaaggccagg tgtccggaat gcccaacgac ccaagccccc tgcaagtggc tgtgaagacg   420
ctgcctgaag tgtgctctga acaggacgaa ctggatttcc tcatggaagc cctgatcatc   480
agcaaattca accaccagaa cattgttcgc tgcattgggg tgagcctgca atccctgccc   540
```

<210> SEQ ID NO 33
<211> LENGTH: 1260
<212> TYPE: DNA
<213> ORGANISM: Artificial Sequence
<220> FEATURE:
<223> OTHER INFORMATION: oligonucleotide

<400> SEQUENCE: 33

```
gggaaatatg aaaagccaaa atttgtgcag tgtttagcat tcttggggaa tggagatgtt    60
cttactggag actcaggtgg agtcatgctt atatggagca aaactactgt agagcccaca   120
cctgggaaag gacctaaagg tgtatatcaa atcagcaaac aaatcaaagc tcatgatggc   180
agtgtgttca cactttgtca gatgagaaat gggatgttat taactggagg agggaaagac   240
agaaaaataa ttctgtggga tcatgatctg aatcctgaaa gagaaataga ggttcctgat   300
cagtatggca caatcagagc tgtagcagaa ggaaaggcag atcaatttt agtaggcaca   360
tcacgaaact ttatttacg aggaacattt aatgatggct ccaaatagaa gtacagggt   420
catacagatg agctttgggg tcttgccaca catcccttca agatttgct cttgacatgt   480
gctcaggaca ggcaggtgtg cctgtggaac tcaatggaac acaggctgga atggaccagg   540
ctggtagatg aaccaggaca ctgtgcagat tttcatccaa gtggcacagt ggtggccata   600
ggaacgcact caggcaggtg gtttgttctg gatgcagaaa ccagagatct agtttctatc   660
cacacagacg ggaatgaaca gctctctgtg atgcgctact caatagatgg taccttcctg   720
gctgtaggat ctcatgacaa ctttatttac ctctctatgt ag tctctgaaaa tggaagaaaa   780
tatagcagat atggaaggtg cactggacat tccagctaca tcacacacct tgactggtcc   840
ccagacaaca gtatataat gtctaactcg ggagactatg aaatattgta cttgtaccgc   900
cggaagcacc aggagctgca agccatgcag atggagctgc agagccctga gtacaagctg   960
agcaagctcc gcacctcgac catcatgacc gactacaacc ccaactactg ctttgctggc  1020
aagacctcct ccatcagtga cctgaaggag gtgccgcgga aaaacatcac cctcattcgg  1080
ggtctgggcc atggagcctt tggggaggtg tatgaaggcc aggtgtccgg aatgcccaac  1140
```

| | |
|---|---|
| gacccaagcc ccctgcaagt ggctgtgaag acgctgcctg aagtgtgctc tgaacaggac | 1200 |
| gaactggatt tcctcatgga agccctgatc atcagcaaat tcaaccacca gaacattgtt | 1260 |

<210> SEQ ID NO 34
<211> LENGTH: 960
<212> TYPE: DNA
<213> ORGANISM: Artificial Sequence
<220> FEATURE:
<223> OTHER INFORMATION: oligonucleotide

<400> SEQUENCE: 34

| | |
|---|---|
| tgatgttcaa gatcgcctgt cagctcttga gtcacgagtt cagcaacaag aagatgaaat | 60 |
| cactgtgcta aaggcggctt tggctgatgt tttgaggcgt cttgcaatct ctgaagatca | 120 |
| tgtggcctca gtgaaaaaat cagtctcaag taaaggccaa ccaagccctc gagcagttat | 180 |
| tcccatgtcc tgtataacca atggaagtgg tgcaaacaga aaaccaagtc ataccagtgc | 240 |
| tgtctcaatt gcaggaaaag aaactctttc atctgctgct aaaagtggta cagaaaaaaa | 300 |
| gaaagaaaaa ccacaaggac agagagaaaa aaaagaggaa tctcattcta atgatcaaag | 360 |
| tccacaaatt cgagcatcac cttctcccca gccctcttca caacctctcc aaatacacag | 420 |
| acaaactcca gaaagcaaga atgctactcc caccaaaagc ataaaacgac catcaccagc | 480 |
| tgaaaagtca cataattctt gggaaaattc agatgatagc cgtaataaat tgtcgaaaat | 540 |
| accttcaaca cccaaattaa taccaaaagt taccaaaact gcagacaagc ataaagatgt | 600 |
| catcatcaac caagtgtacc gccggaagca ccaggagctg caagccatgc agatggagct | 660 |
| gcagagccct gagtacaagc tgagcaagct ccgcacctcg accatcatga ccgactacaa | 720 |
| ccccaactac tgctttgctg caagacctc ctccatcagt gacctgaagg aggtgccgcg | 780 |
| gaaaaacatc accctcattc ggggtctggg ccatggagcc tttggggagg tgtatgaagg | 840 |
| ccaggtgtcc ggaatgccca cgacccaag ccccctgcaa gtggctgtga agacgctgcc | 900 |
| tgaagtgtgc tctgaacagg acgaactgga tttcctcatg aagccctga tcatcagcaa | 960 |

<210> SEQ ID NO 35
<211> LENGTH: 1000
<212> TYPE: DNA
<213> ORGANISM: Artificial Sequence
<220> FEATURE:
<223> OTHER INFORMATION: oligonucleotide

<400> SEQUENCE: 35

| | |
|---|---|
| tgatgttcaa gatcgcctgt cagctcttga gtcacgagtt cagcaacaag aagatgaaat | 60 |
| cactgtgcta aaggcggctt tggctgatgt tttgaggcgt cttgcaatct ctgaagatca | 120 |
| tgtggcctca gtgaaaaaat cagtctcaag taaaggccaa ccaagccctc gagcagttat | 180 |
| tcccatgtcc tgtataacca atggaagtgg tgcaaacaga aaaccaagtc ataccagtgc | 240 |
| tgtctcaatt gcaggaaaag aaactctttc atctgctgct aaaagtggta cagaaaaaaa | 300 |
| gaaagaaaaa ccacaaggac agagagaaaa aaaagaggaa tctcattcta atgatcaaag | 360 |
| tccacaaatt cgagcatcac cttctcccca gccctcttca caacctctcc aaatacacag | 420 |
| acaaactcca gaaagcaaga atgctactcc caccaaaagc ataaaacgac catcaccagc | 480 |
| tgaaaagtca cataattctt gggaaaattc agatgatagc cgtaataaat tgtcgaaaat | 540 |
| accttcaaca cccaaattaa taccaaaagt taccaaaact gcagacaagc ataaagatgt | 600 |
| catcatcaac caagcaaaaa tgtcaactcg cgaaaaaaac agccaagtgt accgccggaa | 660 |
| gcaccaggag ctgcaagcca tgcagatgga gctgcagagc cctgagtaca agctgagcaa | 720 |

```
gctccgcacc tcgaccatca tgaccgacta caaccccaac tactgctttg ctggcaagac    780
ctcctccatc agtgacctga aggaggtgcc gcggaaaaac atcaccctca ttcggggtct    840
gggccatgga gcctttgggg aggtgtatga aggccaggtg tccggaatgc ccaacgaccc    900 aagcccctg caagtggctg tgaagacgct gcctgaagtg tgctctgaac aggacgaact     960
ggatttcctc atggaagccc tgatcatcag caaattcaac                          1000

<210> SEQ ID NO 36
<211> LENGTH: 342
<212> TYPE: DNA
<213> ORGANISM: Artificial Sequence
<220> FEATURE:
<223> OTHER INFORMATION: oligonucleotide

<400> SEQUENCE: 36
aatctcatat tttcttctgg acctggagcg gcaattcact aacaagaaaa cagggaattt     60
ttgggaaata tgaaaagcca aaatttgtgc agtgtttagc attcttgggg aatggagatg    120
ttcttactgg agactcaggt ggagtcatgc ttatatggag caaaactact gtagagccca    180
cacctgggaa aggacctaaa ggaagtggcc tgtgtagtgc ttcaagggcc aggctgccag    240
gccatgttgc agctgaccac ccacctgcag tgtaccgccg aagcaccag gagctgcaag    300 ccatgcagat ggagctgcag agccctgagt acaagctgag ca                       342

<210> SEQ ID NO 37
<211> LENGTH: 342
<212> TYPE: DNA
<213> ORGANISM: Artificial Sequence
<220> FEATURE:
<223> OTHER INFORMATION: oligonucleotide

<400> SEQUENCE: 37
acagatgagc tttgggggtct tgccacacat cccttcaaag atttgctctt gacatgtgct    60
caggacaggc aggtgtgcct gtggaactca atggaacaca ggctggaatg gaccaggctg   120
gtagatgaac caggacactg tgcagatttt catccaagtg gcacagtggt ggccatagga   180
acgcactcag gcaggccatg ttgcagctga ccacccacct gcagtgtacc gccggaagca   240
ccaggagctg caagccatgc agatggagct gcagagccct gagtacaagc tgagcaagct   300
ccgcacctcg accatcatga ccgactacaa ccccaactac tg                       342

<210> SEQ ID NO 38
<211> LENGTH: 342
<212> TYPE: DNA
<213> ORGANISM: Artificial Sequence
<220> FEATURE:
<223> OTHER INFORMATION: oligonucleotide

<400> SEQUENCE: 38
caggcaggtg tgcctgtgga actcaatgga acacaggctg gaatggacca ggctggtaga    60
tgaaccagga cactgtgcag attttcatcc aagtggcaca gtggtggcca taggaacgca   120
ctcaggcagg agacaaaaac atgaagtcaa ttttcccaaa attaaactca ttaaaaaatg   180
tggaatgctg ccaggccatg ttgcagctga ccacccacct gcagtgtacc gccggaagca   240
ccaggagctg caagccatgc agatggagct gcagagccct gagtacaagc tgagcaagct   300
ccgcacctcg accatcatga ccgactacaa ccccaactac tg                       342

<210> SEQ ID NO 39
```

<211> LENGTH: 342
<212> TYPE: DNA
<213> ORGANISM: Artificial Sequence
<220> FEATURE:
<223> OTHER INFORMATION: oligonucleotide

<400> SEQUENCE: 39

```
caaatcaaag ctcatgatgg cagtgtgttc acactttgtc agatgagaaa tgggatgtta    60
ttaactggag gagggaaaga cagaaaaata attctgtggg atcatgatct gaatcctgaa   120
agagaaatag agatatgctg gatgagccct gagtacaagc tgagcaagct ccgcacctcg   180
accatcatga ccgactacaa ccccaactac tgctttgctg gcaagacctc ctccatcagt   240
gacctgaagg aggtgccgcg gaaaaacatc accctcattc ggggtctggg ccatggagcc   300
tttggggagg tgtatgaagg ccaggtgtcc ggaatgccca ac                      342
```

<210> SEQ ID NO 40
<211> LENGTH: 650
<212> TYPE: DNA
<213> ORGANISM: Artificial Sequence
<220> FEATURE:
<223> OTHER INFORMATION: oligonucleotide

<400> SEQUENCE: 40

```
gggaaatatg aaaagccaaa atttgtgcag tgtttagcat tcttggggaa tggagatgtt    60
cttactggag actcaggtgg agtcatgctt atatggagca aaactactgt agagcccaca   120
cctgggaaag gacctaaagg tgtatatcaa atcagcaaac aaatcaaagc tcatgatggc   180
agtgtgttca cactttgtca gatgagaaat gggatgttat taactggagg agggaaagac   240
agaaaaataa ttctgtggga tcatgatctg aatcctgaaa gagaaatagg gttcctgat   300
cagtatggca caatcagagc tgtagcagaa ggaaaggcag atcaatttt agtaggcaag   360
ctccgcacct cgaccatcat gaccgactac aaccccaact actgctttgc tggcaagacc   420
tcctccatca gtgacctgaa ggaggtgccg cggaaaaaca tcaccctcat tcggggtctg   480
ggccatggag cctttgggga ggtgtatgaa ggccaggtgt ccggaatgcc aacgaccca   540
agcccctgc aagtggctgt gaagacgctg cctgaagtgt gctctgaaca ggacgaactg   600
gatttcctca tggaagccct gatcatcagc aaattcaacc accagaacat             650
```

<210> SEQ ID NO 41
<211> LENGTH: 342
<212> TYPE: DNA
<213> ORGANISM: Artificial Sequence
<220> FEATURE:
<223> OTHER INFORMATION: oligonucleotide

<400> SEQUENCE: 41

```
ttctgctgca agtacttctg atgttcaaga tcgcctgtca gctcttgagt cacgagttca    60
gcaacaagaa gatgaaatca ctgtgctaaa ggcggctttg gctgatgttt tgaggcgtct   120
tgcaatctct gaagatcatg tggcctcagt gaaaaaatca gtctcaagta agtgtaccg   180
ccggaagcac caggagctgc aagccatgca gatggagctg cagagccctg agtacaagct   240
gagcaagctc cgcacctcga ccatcatgac cgactacaac cccaactact gctttgctgg   300
caagacctcc tccatcagtg acctgaagga ggtgccgcgg aa                      342
```

<210> SEQ ID NO 42
<211> LENGTH: 650
<212> TYPE: DNA
<213> ORGANISM: Artificial Sequence
<220> FEATURE:
<223> OTHER INFORMATION: oligonucleotide

<400> SEQUENCE: 42

```
atttctgctg caagtacttc tgatgttcaa gatcgcctgt cagctcttga gtcacgagtt      60
cagcaacaag aagatgaaat cactgtgcta aggcggctt tggctgatgt tttgaggcgt     120
cttgcaatct ctgaagatca tgtggcctca gtgaaaaaat cagtctcaag taaaggttca     180
gagctcaggg gaggatatgg agatccaggg aggcttcctg taggaagtgg cctgtgtagt     240
gcttcaaggg ccaggctgcc aggccatgtt gcagctgacc acccacctgc agtgtaccgc     300
cggaagcacc aggagctgca agccatgcag atggagctgc agagccctga gtacaagctg     360
agcaagctcc gcacctcgac catcatgacc gactacaacc ccaactactg ctttgctggc     420
aagacctcct ccatcagtga cctgaaggag gtgccgcgga aaaacatcac cctcattcgg     480
ggtctgggcc atggagcctt tggggaggtg tatgaaggcc aggtgtccgg aatgcccaac     540
gacccaagcc ccctgcaagt ggctgtgaag acgctgcctg aagtgtgctc tgaacaggac     600
gaactggatt tcctcatgga agccctgatc atcagcaaat caaccacca              650
```

<210> SEQ ID NO 43
<211> LENGTH: 342
<212> TYPE: DNA
<213> ORGANISM: Artificial Sequence
<220> FEATURE:
<223> OTHER INFORMATION: oligonucleotide

<400> SEQUENCE: 43

```
agcaaaacta ctgtagagcc cacacctggg aaaggaccta aggtgtata tcaaatcagc      60
aaacaaatca agctcatga tggcagtgtg ttcacacttt gtcagatgag aaatgggatg     120
ttattaactg gaggagggaa agacagaaaa ataattctgt gggatcatga tctgaatcct     180
gaaagagaaa tagagcacca ggagctgcaa gccatgcaga tggagctgca gagccctgag     240
tacaagctga gcaagctccg cacctcgacc atcatgaccg actacaaccc caactactgc     300
tttgctggca agacctcctc catcagtgac ctgaaggagg tg                       342
```

<210> SEQ ID NO 44
<211> LENGTH: 1050
<212> TYPE: DNA
<213> ORGANISM: Artificial Sequence
<220> FEATURE:
<223> OTHER INFORMATION: oligonucleotide

<400> SEQUENCE: 44

```
aaagccaaaa tttgtgcagt gtttagcatt cttggggaat ggagatgttc ttactggaga      60
ctcaggtgga gtcatgctta tatggagcaa aactactgta gagcccacac ctgggaaagg     120
acctaaaggt gtatatcaaa tcagcaaaca aatcaaagct catgatggca gtgtgttcac     180
actttgtcag atgagaaatg ggatgttatt aactggagga gggaaagaca gaaaaataat     240
tctgtgggat catgatctga atcctgaaag agaaatagag gttcctgatc agtatggcac     300
aatcagagct gtagcagaag gaaaggcaga tcaattttta gtaggcacat cacgaaactt     360
tattttacga ggaacattta atgatggctt ccaaatagaa gtacagggtc atacagatga     420
gctttgggt cttgccacac atcccttcaa agatttgctc ttgacatgtg ctcaggacag     480
gcaggtgtgc ctgtggaact caatggaaca caggctggaa tggaccaggc tggtagatga     540
accaggacac tgtgcagatt tcatccaag tggcacagtg gtggccatag gaacgcactc     600
```

| | |
|---|---|
| aggcaggtgg tttgttctgg atgcagaaac cagagatcta gtttctatcc acacagacgg | 660 |
| gaatgaacag ctctctgtga tgcgctactc aatagtgtac cgccggaagc accaggagct | 720 |
| gcaagccatg cagatggagc tgcagagccc tgagtacaag ctgagcaagc tccgcacctc | 780 |
| gaccatcatg accgactaca accccaacta ctgctttgct ggcaagacct cctccatcag | 840 |
| tgacctgaag gaggtgccgc ggaaaaacat caccctcatt cggggtctgg ccatggagc | 900 |
| ctttggggag gtgtatgaag gccaggtgtc cggaatgccc aacgacccaa gcccctgca | 960 |
| agtggctgtg aagacgctgc ctgaagtgtg ctctgaacag gacgaactgg atttcctcat | 1020 |
| ggaagccctg atcatcagca aattcaacca | 1050 |

```
<210> SEQ ID NO 45
<211> LENGTH: 342
<212> TYPE: DNA
<213> ORGANISM: Artificial Sequence
<220> FEATURE:
<223> OTHER INFORMATION: oligonucleotide

<400> SEQUENCE: 45
```

| | |
|---|---|
| gcgacttcga gctacagctg agagagtgaa agctttggaa tcagcactga agaagctaa | 60 |
| agaaaatgca tctcgtgatc gcaaacgcta tcagcaagaa gtagatcgca taaaggaagc | 120 |
| agtcaggtca agaatatgg ccagaagagg gcattctgca cagattgtgt accgccggaa | 180 |
| gcaccaggag ctgcaagcca tgcagatgga gctgcagagc cctgagtaca agctgagcaa | 240 |
| gctccgcacc tcgaccatca tgaccgacta caaccccaac tactgctttg ctggcaagac | 300 |
| ctcctccatc agtgacctga aggaggtgcc gcggaaaaac at | 342 |

```
<210> SEQ ID NO 46
<211> LENGTH: 322
<212> TYPE: DNA
<213> ORGANISM: Artificial Sequence
<220> FEATURE:
<223> OTHER INFORMATION: oligonucleotide

<400> SEQUENCE: 46
```

| | |
|---|---|
| ccaaccacca gaaaaaacga gcagctgaga tgatggcatc tttactaaaa gaccttgcag | 60 |
| aaataggaat tgctgtggga ataatgatg taaagccaac caccagaaaa aacgagcagc | 120 |
| tgagatgatg gcatctttac taaaagacct tgcagaaata ggaattgctg tgggaaataa | 180 |
| tgatgtaaag caccaggagc tgcaagccat gcagatggag ctgcagagcc ctgagtacaa | 240 |
| gctgagcaag ctccgcacct cgaccatcat gaccgactac aaccccaact actgctttgc | 300 |
| tggcaagacc tcctccatca gt | 322 |

```
<210> SEQ ID NO 47
<211> LENGTH: 322
<212> TYPE: DNA
<213> ORGANISM: Artificial Sequence
<220> FEATURE:
<223> OTHER INFORMATION: oligonucleotide

<400> SEQUENCE: 47
```

| | |
|---|---|
| caaaaaaatg aagaaaatg aaaggagtt agcagcatgt cagcttcgta tctctcaaca | 60 |
| tgaagccaaa atcaagtcat tgactgaata ccttcaaaat gtggaacaaa agaaaagaca | 120 |
| gttggaggaa tctgtcgatg ccctcagtga agaactagtc cagcttcgag cacaagtgta | 180 |
| ccgccggaag caccaggagc tgcaagccat gcagatggag ctgcagagcc ctgagtacaa | 240 |
| gctgagcaag ctccgcacct cgaccatcat gaccgactac aaccccaact actgctttgc | 300 |

```
tggcaagacc tcctccatca gt                                           322

<210> SEQ ID NO 48
<211> LENGTH: 342
<212> TYPE: DNA
<213> ORGANISM: Artificial Sequence
<220> FEATURE:
<223> OTHER INFORMATION: oligonucleotide

<400> SEQUENCE: 48
aaccagggca agtatgaaga agtagaatat tattatcaaa gagccctcga gatctaccag    60
acaaaactgg gacctgatga ccccaacgtg gctaagacga aaaataacct ggcatcctgc   120
tatttgaaac aaggaaagtt caagcaagca gaaacactgt acaaagagat tctcactcgt   180
gcacatgaaa gggagtttgg ttctgtagat gtgtaccgcc ggaagcacca ggagctgcaa   240
gccatgcaga tggagctgca gagccctgag tacaagctga gcaagctccg cacctcgacc   300
atcatgaccg actacaaccc caactactgc tttgctggca ag                     342

<210> SEQ ID NO 49
<211> LENGTH: 342
<212> TYPE: DNA
<213> ORGANISM: Artificial Sequence
<220> FEATURE:
<223> OTHER INFORMATION: oligonucleotide

<400> SEQUENCE: 49
tgaaactgac attatttgtt aatggccagc caagacccct tgaatcaagt caggtgaaat    60
atctccgtcg agaactgata gaacttcgaa ataaagtgaa tcgtttattg gatagcttgg   120
aaccacctgg agaaccagga ccttccacca atattcctga aaatgtgtac cgccggaagc   180
accaggagct gcaagccatg cagatggagc tgcagagccc tgagtacaag ctgagcaagc   240
tccgcacctc gaccatcatg accgactaca ccccaactac tgctttgct ggcaagacct   300 cctccatcag tgacctgaag gaggtgccgc ggaaaaacat ca                     342
```

PRIMER REAGENT FOR AMPLIFYING ALK FUSION GENE, ALK FUSION GENE AMPLIFICATION REAGENT KIT INCLUDING THE SAME, AND ALK FUSION GENE AMPLIFICATION METHOD AND ALK FUSION GENE ANALYSIS METHOD USING THE SAME

A computer readable text file, entitled "SequenceListing.txt," created on or about Oct. 29, 2015 with a file size of about 21 kb contains the sequence listing for this application and is hereby incorporated by reference in its entirety.

BACKGROUND OF THE INVENTION

1. Field of the Invention

The present invention relates to a primer reagent for amplifying an ALK fusion gene, an ALK fusion gene amplification reagent kit including the same, and an ALK fusion gene amplification method and ALK fusion gene analysis method using the same.

2. Description of Related Art

ALK (Anaplastic Limphoma Kinase) is one type of kinase. It is known that an ALK fusion gene is formed as a result of rearrangement or translocation of the ALK gene coding for ALK with another gene. The ALK fusion gene is known to be involved in lung cancer. Also, kinase inhibitors are effective as anticancer drugs for lung cancer in which the ALK fusion gene is involved. Thus, by analyzing whether the ALK gene in a patient is an ALK fusion gene or not, for example, the probability that the patient may have or develop lung cancer may be determined, or when the patient has lung cancer, as a treatment method, the use of a kinase inhibitor, the amount of the kinase inhibitor to be used, or changing of the kinase inhibitor to another therapeutic agent may be determined.

Examples of the ALK fusion gene include: EML4-ALK as a fusion gene with the EML4 (Echinoderm Microtubule-associated protein-Like 4) gene; KIF5B-ALK as a fusion gene with the KIF5B (Kinesin Family member 5B) gene; KLC1-ALK as a fusion gene with the KLC1 (Kinesin Light Chain 1) gene; and TFG-ALK as a fusion gene with the TFG gene (TRK-fused gene) (Patent Documents 1 to 4). Among them, variants V1, V2, V3a, V3b, and V6 of the EML4-ALK are seen in about 70% of lung cancer patients expressing the ALK fusion gene. Thus, simplifying the analysis process of these variants is useful in diagnosis and treatment of lung cancer.

A genetic testing method generally is carried out by, for example, causing nucleic acid amplification, such as PCR (Polymerase Chain Reaction), using a primer that anneals to a specific region in a target gene and determining the presence or absence of the target gene on the basis of whether or not the amplification occurred. When the target gene has a plurality of variants as described above, however, it requires cumbersome operations of providing primers for the respective variants to prepare reaction systems for the respective variants and checking the presence or absence of each one of the variants.

CITATION LIST

Patent Document(s)

Patent Document 1: Japanese Patent No. 4303303
Patent Document 2: JP 2010-501175 A
Patent Document 3: WO 2011/087709
Patent Document 4: JP 2012-100628 A

BRIEF SUMMARY OF THE INVENTION

Problem to be Solved by the Invention

With the foregoing in mind, it is an object of the present invention to provide a novel primer reagent for detecting a plurality of variants of the ALK fusion gene easily through gene amplification in one reaction system.

Means for Solving Problem

In order to achieve the above object, the present invention provides a primer reagent for an ALK fusion gene, including:

a forward primer consisting of the nucleotide sequence of SEQ ID NO: 1 (F_V1/6);
a forward primer consisting of the nucleotide sequence of SEQ ID NO: 2;
a forward primer consisting of the nucleotide sequence of SEQ ID NO: 3 (F_V3a);
a forward primer consisting of the nucleotide sequence of SEQ ID NO: 4 (F_V3b);
a reverse primer consisting of the nucleotide sequence of SEQ ID NO: 5 (R_V/multi); and
a reverse primer consisting of the nucleotide sequence of SEQ ID NO: 6 (R_V6).

The present invention also provides an amplification reagent kit for an ALK fusion gene, including: the primer reagent according to the present invention.

The present invention also provides an amplification method for amplifying an ALK fusion gene, including the step of: amplifying a template nucleic acid in one reaction system including the primer reagent according to the present invention.

The present invention also provides an analysis method for analyzing an ALK fusion gene, including the steps of: amplifying a template nucleic acid in a test sample by the amplification method according to the present invention; and detecting an ALK fusion gene in the test sample by detecting amplification of the template nucleic acid.

The present invention also provides an analysis reagent kit for an ALK fusion gene, including: the primer reagent according to the present invention.

The present invention also provides a test method for testing efficacy (or sensitivity) of a drug, including the steps of: analyzing an ALK fusion gene by the analysis method according to the present invention; and testing sensitivity to (or efficacy of) the drug on the basis of the presence or absence of the ALK fusion gene.

Effects of the Invention

According to the primer reagent of the present invention, variants V1, V2, V3a, V3b, and V6 of the ALK fusion gene can be amplified at the same time in the same reaction system. Thus, according to the present invention, two or more types of variants of the ALK fusion gene can be detected easily with the use of one reaction system. Therefore, the present invention is useful in diagnosis of the possibility of lung cancer and treatment of lung cancers, for example.

DETAILED DESCRIPTION OF THE INVENTION

Figure 1:
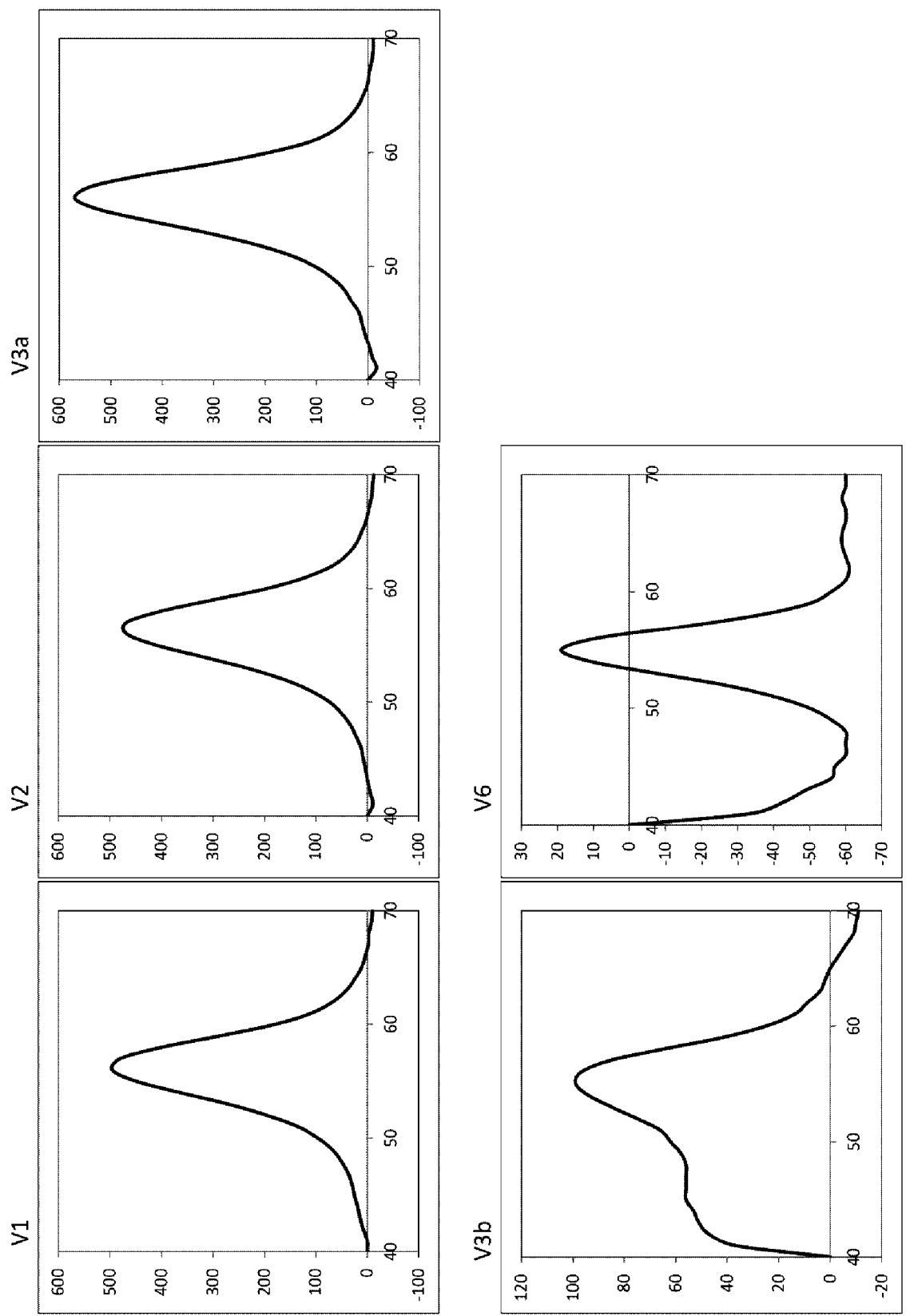
FIG. 1 shows graphs of Tm analysis results obtained in Example A1 of the present invention.

The primer reagent of the present invention further includes, for example:
a forward primer consisting of the nucleotide sequence of SEQ ID NO: 7 (F_V8a);
a forward primer consisting of the nucleotide sequence of SEQ ID NO: 8 (F_V8b);
a forward primer consisting of the nucleotide sequence of SEQ ID NO: 9 (F_V4);
a forward primer consisting of the nucleotide sequence of SEQ ID NO: 10 (F_V4');
a reverse primer consisting of the nucleotide sequence of SEQ ID NO: 11 (R_V8a/b); and
a reverse primer consisting of the nucleotide sequence of SEQ ID NO: 12 (R_V4/4').

The primer reagent of the present invention further includes, for example:
a forward primer consisting of the nucleotide sequence of SEQ ID NO: 13 (F_V5a/b);
a forward primer consisting of the nucleotide sequence of SEQ ID NO: 14 (F_V7);
a forward primer consisting of the nucleotide sequence of SEQ ID NO: 15 (F_V9);
a reverse primer consisting of the nucleotide sequence of SEQ ID NO: 5 (R_V/multi); and
a reverse primer consisting of the nucleotide sequence of SEQ ID NO: 16 (R_V5b).

The primer reagent of the present invention further includes, for example:
a forward primer consisting of the nucleotide sequence of SEQ ID NO: 17 (F_KIF/e24);
a forward primer consisting of the nucleotide sequence of SEQ ID NO: 18 (F_KIF/e15);
a forward primer consisting of the nucleotide sequence of SEQ ID NO: 19 (F_KIF/e17);
a forward primer consisting of the nucleotide sequence of SEQ ID NO: 20 (F_KLC1);
a forward primer consisting of the nucleotide sequence of SEQ ID NO: 21 (F_TFG); and
a reverse primer consisting of the nucleotide sequence of SEQ ID NO: 5 (R_V/multi).

The ALK fusion gene analysis method according to the present invention may be configured so that, for example, in the detection step, the amplification of the template nucleic acid is detected using a probe.

The ALK fusion gene analysis method according to the present invention may be configured so that, for example, the detection using the probe is melting curve analysis.

The analysis reagent kit according to the present invention may further include a probe that hybridizes to an amplification product produced using the primer reagent, for example.

In the present invention, a forward primer hereinafter also is referred to as "F primer", and a reverse primer hereinafter also is referred to as "R primer".

The ALK fusion gene generally means a fusion gene that occurs as a result of rearrangement or translocation of the ALK gene. Examples of the ALK fusion gene include: EML4-ALK as a fusion gene of the ALK gene and EML4 gene; KIF5B-ALK as a fusion gene of the ALK gene and the KIF5B gene; KLC1-ALK as a fusion gene of the ALK gene and KLC1 gene; and TFG-ALK as a fusion gene of the ALK gene and the TFG gene.

EML4-ALK as the ALK fusion gene has variants shown in the following tables, for example. In the following tables, "E followed by a numeral" indicates the exon number where the fusion occurs in the EML4 gene, and "A followed by a numeral" indicates the exon number where the fusion occurs in the ALK gene. For example, "E13; A20" in V1 means that exon 13 of the EML4 gene is fused to exon 20 of the ALK gene. Furthermore, "ins followed by a numeral" indicates the presence of an insertion sequence on the upstream side from exon 20 of the ALK gene and the length (base length) of the insertion sequence. For example, "E6; ins69 A20" in V6 means that exon 6 of the EML4 gene is fused to exon 20 of the ALK gene via a 69-mer insertion sequence. Still further, "del followed by a numeral" indicates the presence of deletion on the upstream side in exon 20 of the ALK gene and the length (base length) of the deleted sequence. For example, "E14; del12 A20" in V7 means that exon 14 of the EML4 gene is fused to exon 20, having deletion of 12 bases on the upstream side, of the ALK gene. As shown in Tables 1 to 3 below, the respective variants are identified in various scientific literatures or registered in the database GenBank under the following accession numbers, for example. Among variants of the ALK fusion gene, five types of variants V1, V2, V3a, V3b, and V6 forms a major marker group seen in about 70% of lung cancer cases in which the ALK fusion gene is involved.

TABLE 1

EML-ALK

| Variant | Fusion Site | Accession No. or Literature |
| --- | --- | --- |
| V1 | E13; A20 | AB274722.1 |
| V2 | E20; A20 | AB275889.1 |
| V3a | E6; A20 | AB374361.1 |
| V3b | E6; A20 | AB374362.1 |
| V4 | E14; A20 | AB374363.1 |
| V4' | E15 del19; del20 A20 | Clin Cancer Res 2008; 14(13), 4275-83 |
| V5a | E2; A20 | AB374364.1 |
| V5b | E2; ins17 A20 | AB374365.1 |
| V6 | E13; ins69 A20 | AB462411.1 |
| V8a | E17; ins30 A20 | GU797894.1 |
| V8b | E17; ins95 A20 | GU797895.1 |
| V7 | E14; del12 A20 | AB663645.1 |
| V9 | E18; A20 | Cancer 2009; 115: 1723-33 |

TABLE 2

KIF5B-ALK

| Variant | Fusion Site | Accession No. or Literature |
| --- | --- | --- |
| KIF5B exon24-ALK | exon 24 of KIF5B and A20 | AB462413 |
| KIF5B exon15-ALK | exon 15 of KIF5B and A20 | Cancer 2011; 117: 2709-2718 |
| KIF5B exon17-ALK | exon 17 of KIF5B and A20 | AB795238 |

TABLE 3

Other fusion genes

| Variant | Fusion Site | Accession No. or Literature |
| --- | --- | --- |
| KLC1-ALK | exon 9 of KLC1 and A20 | AB781674.1 |
| TFG-ALK | exon 3 of TFG and A20 | Nature 2007; 448: 561-566 |

In the present invention, the numerical range delimited by a maximum value and a minimum value discloses, for example, all the numerical values present between the maximum value and the minimum value. For example, the description "1 to 5 bases" means all of "1, 2, 3, 4, and 5 bases".

(1) Primer Reagent

As described above, the primer reagent of the present invention is characterized in that it includes:
the F primer consisting of the oligonucleotide SEQ ID NO: 1 (F_V1/6);
the F primer consisting of the oligonucleotide SEQ ID NO: 2 (F_V2);
the F primer consisting of the oligonucleotide SEQ ID NO: 3 (F_V3a);
the F primer consisting of the oligonucleotide SEQ ID NO: 4 (F_V3b);
the R primer consisting of the oligonucleotide SEQ ID NO: 5 (R_V/multi); and
the R primer consisting of the oligonucleotide SEQ ID NO: 6 (R_V6).

```
(F_V1/6): the oligonucleotide consisting of the
base sequence of SEQ ID NO: 1
                                      (SEQ ID NO: 1)
5'-cctgggaaaggacctaaag-3'

(F_V2): the oligonucleotide consisting of the base
sequence of SEQ ID NO: 2
                                      (SEQ ID NO: 2)
5'-gggagactatgaaatattgtacttg-3'

(F_V3a): the oligonucleotide consisting of the
base sequence of SEQ ID NO: 3
                                      (SEQ ID NO: 3)
5'-ataaagatgtcatcatcaaccaag-3'

(F_V3b): the oligonucleotide consisting of the
base sequence of SEQ ID NO: 4
                                      (SEQ ID NO: 4)
5'-gcgaaaaaaacagccaag-3'

(R_V/multi): the oligonucleotide consisting of the
base sequence of SEQ ID NO: 5
                                      (SEQ ID NO: 5)
5'-gctccatctgcatggc-3'

(R_V6): the oligonucleotide consisting of the base
sequence of SEQ ID NO: 6
                                      (SEQ ID NO: 6)
5'-tggcagcctggccc-3'
```

Variants of these oligonucleotides may also be used as described hereinbelow. Preferably, the primers consist of the oligonucleotides described herein.

According to the primer reagent of the present invention, it is possible to amplify major variants V1, V2, V3a, V3b, and V6 of the ALK fusion gene at the same time in the same reaction system including the primer reagent, for example. Thus, according to the primer reagent of the present invention, at least the above-described five types of major variants can be analyzed merely by causing amplification reactions in one reaction system using the primer reagent.

Generally, a primer for amplifying a variant of a fusion gene is designed so as to amplify a region of about 1000-mer. In contrast, the F primers and the R primers in the primer reagent of the present invention are designed so that they amplify relatively short regions including the fusion points of the respective variants, respectively. In some embodiments, the short regions may be from 10, 20, 30, 40, 50, 60 or 70 to 120, 130, 140, 150, 160, 170, or 200-mer. For example, when a target is RNA in a sample, the RNA is degraded easily in the sample. Even if the RNA is fragmented, however, the F primers and the R primers, which are designed so as to amplify relatively short regions as described above, can achieve amplification of the target regions including the fusion points without being influenced by the fragmentation.

The F primer (F_V1/6) is a primer that anneals to exon 13 of the EML4 gene. The F primer (F_V2) is a primer that anneals to a region extending from the 23rd base counted toward the upstream side from the fusion point at exon 20 of the EML4 gene to the 2nd base counted toward the downstream side from the fusion point at exon 20 of the ALK gene. The F primer (F_V3a) is a primer that anneals to a region extending from the 24th base counted toward the upstream side from the fusion point at exon 6 of the EML4 gene to the 1st base counted toward the downstream side from the fusion point at exon 20 of the ALK gene. The F primer (F_V3b) is a primer that anneals to a region extending from the 18th base counted toward the upstream side from the fusion point at exon 6 of the EML4 gene to the 1st base counted toward the downstream side from the fusion point at exon 20 of the ALK gene. The R primer (R_V/multi) is a primer that anneals to exon 20 of the ALK gene. The R primer (R_V6) is a primer that anneals to an insertion region adjacent to the upstream of exon 20 of the ALK gene.

With the F primer (F_V1/6) and the R primer (R_V/multi), a region including the fusion point of the EML4 gene and the ALK gene in the V1 can be amplified, and the length of the amplified fragment is, for example, about 64 bp including the regions of the respective primers. With the F primer (F_V2) and the R primer (R_V/multi), a region including the fusion point of the EML4 gene and the ALK gene in the V2 can be amplified, and the length of the amplified fragment is, for example, about 88 bp including the regions of the respective primers. With the F primer (F_V3a) and the R primer (R_V/multi), a region including the fusion point of the EML4 gene and the ALK gene in the V3a can be amplified, and the length of the amplified fragment is, for example, about 69 bp including the regions of the respective primers. With the F primer (F_V3b) and the R primer (R_V/multi), a region including the fusion point of the EML4 gene and the ALK gene in the V3b can be amplified, and the length of the amplified fragment is, for example, about 63 bp including the regions of the respective primers. With the F primer (F_V1/6) and the R primer (R_V6), a region including the fusion point of the EML4 gene and the ALK gene in the V6 can be amplified, and the length of the amplified fragment is, for example, about 63 bp including the regions of the respective primers.

According to the primer reagent of the present invention, five types of variants of the ALK fusion gene, namely, V1, V2, V3a, V3b, and V6, can be amplified at the same time in one reaction system including all these primers, for example. Thus, at least the five types of the major variants of the ALK fusion gene can be analyzed, detected, or quantified by carrying out amplification using the primer reagent of the present invention and then checking whether or not the amplification occurred or the amount of amplification.

The amount of each of the four types of F primers and the two types of R primers contained in the primer reagent of the present invention is not particularly limited. The ratio (molar ratio F:R) between the molar amount (F) of the F primer and the molar amount (R) of the R primer for one type of variant to be detected thereby is, for example, 1:1 to 1:6. As a specific example, the ratio (molar ratio F:R) between them is 1:6. The total amount of the four types of F primers and the total amount of the two types of R primers contained in the primer reagent of the present invention are not particularly limited.

The four types of F primers and the two types of R primers may form the following primer sets, for example. By using any one of the following primer sets, it is possible to amplify one type of the variant alone. Also, it is possible to amplify, for example, two, three, four, or five types of the variants by combining the following primer sets as appropriate depending on the variants to be detected. As a specific example, when V1 and V2 are to be amplified, the reagent may comprise the combination of the following primer set for V1 and the following primer set for V2, for example. In this case, because both the primer sets have the same R primer, this combination includes two types of F primers and one type of R primer.

Primer set for V1
   the F primer (F_V1/6)
   the R primer (R_V/multi)
Primer set for V2
   the F primer (F_V2)
   the R primer (R_V/multi)
Primer set for V3a
   the F primer (F_V3a)
   the R primer (R_V/multi)
Primer set for V3b
   the F primer (F_V3b)
   the R primer (R_V/multi)
Primer set for V6
   the F primer (F_V1/6)
   the R primer (R_V6)

In the primer reagent of the present invention, the combination of the four types of F primers and the two types of R primers that can amplify the five types of variants (V1, V2, V3a, V3b, and V6) hereinafter also is referred to as "Pack 1 primer reagent.".

The primer reagent of the present invention may comprise only the Pack 1 primer reagent as primers, or it may further include other primers, for example.

Examples of the other primers include the following Pack 2 primer reagent, the following Pack 3 primer reagent, and the following Pack 4 primer reagent.

The Pack 2 primer reagent includes, for example:
the forward primer consisting of the oligonucleotide (F_V8a);
the forward primer consisting of the oligonucleotide (F_V8b);
the forward primer consisting of the oligonucleotide (F_V4);
the forward primer consisting of the oligonucleotide (F_V4');
the reverse primer consisting of the oligonucleotide (R_V8a/b); and
the reverse primer consisting of the oligonucleotide (R_V4/4').

(F_V8a): the oligonucleotide consisting of the base sequence of SEQ ID NO: 7
                            (SEQ ID NO: 7)
5'-ataggaacgcactcaggc-3'

(F_V8b): the oligonucleotide consisting of the base sequence of SEQ ID NO: 8
                            (SEQ ID NO: 8)
5'-aaatgtggaatgctgccag-3'

(F_V4): the oligonucleotide consisting of the base sequence of SEQ ID NO: 9
                            (SEQ ID NO: 9)
5'-gagatatgctggatgagcc-3'

(F_V4'): the oligonucleotide consisting of the base sequence of SEQ ID NO: 10
                            (SEQ ID NO: 10)
5'-gaaggaaaggcagatcaattttag-3'

(R_V8a/b): the oligonucleotide consisting of the base sequence of SEQ ID NO: 11
                            (SEQ ID NO: 11)
5'-tacactgcaggtgggtg-3'

(R_V4/4'): the oligonucleotide consisting of the base sequence of SEQ ID NO: 12
                            (SEQ ID NO: 12)
5'-tgtagtcggtcatgatgg-3'

Variants of these oligonucleotides may also be used as described hereinbelow. Preferably, the primers consist of the oligonucleotides described herein.

The F primer (F_V8a) is a primer that anneals to a region extending from the 21st base counted toward the upstream side from the fusion point at exon 17 of the EML4 gene to the 4th base counted toward the downstream side from the fusion point at exon 20 of the ALK gene. The F primer (F_V8b) is a primer that anneals to an insertion sequence region between the EML4 gene and the ALK gene in the variant 8b of the EML4-ALK fusion gene. The F primer (F_V4) is a primer that anneals to a region extending from the 3rd base counted toward the upstream side from the fusion point at exon 14 of the EML4 gene to the 16th base counted toward the downstream side from the fusion point at exon 20 of the ALK gene. The F primer (F_V4') is a primer that anneals to a region extending from the 30th base counted toward the upstream side from the fusion point at exon 15 of the EML4 gene to the 6th base counted toward the downstream side from the fusion point at exon 20 of the ALK gene. The R primer (R_V8a/b) is a primer that anneals to an insertion region adjacent to the upstream of exon 20 of the ALK gene. The R primer (R_V4/4') is a primer that anneals to exon 20 of the ALK gene.

With the F primer (F_V8a) and the R primer (R_V8a/b), a region including the fusion point of the EML4 gene and the ALK gene in the V8a can be amplified, and the length of the amplified fragment is, for example, about 54 bp including the regions of the respective primers. With the F primer (F_V8b) and the R primer (R_V8a/b), a region including the fusion point of the EML4 gene and the ALK gene in the V8b can be amplified, and the length of the amplified fragment is, for example, about 53 bp including the regions of the respective primers. With the F primer (F_V4) and the R primer (R_V4/4'), a region including the fusion point of the EML4 gene and the ALK gene in the V4 can be amplified, and the length of the amplified fragment is, for example, about 78 bp including the regions of the respective primers. With the F primer (F_V4') and the R primer (R_V4/4'), a region including the fusion point of the EML4 gene and the ALK gene in the V4' can be amplified, and the length of the amplified fragment is, for example, about 64 bp including the regions of the respective primers.

When the primer reagent of the present invention includes the Pack 2 primer reagent in addition to the Pack 1 primer reagent, not only the five types of variants (V1, V2, V3a, V3b, and V6) of the ALK fusion gene but also other four types of variants (V8a, V8b, V4, and V4') can be amplified at the same time in one reaction system including all these primers, for example. Thus, when the primer reagent of the present invention includes the Pack 1 primer reagent and the Pack 2 primer reagent, at least nine types of variants of the ALK fusion gene in total, including the major five types of variants, may be analyzed and detected by checking whether or not the amplification occurred or the amount of amplification.

The amount of each of the four types of F primers and the two types of R primers contained in the Pack 2 primer reagent is not particularly limited. The ratio (molar ratio F:R) between the total molar amount (F) of the F primers and the total molar amount (R) of the R primers is, for example, 1:1 to 1:6. As a specific example, the ratio (molar ratio F:R) between them is 1:6. The total amount of the four types of F primers and the total amount of the two types of R primers contained in the Pack 2 primer reagent are not particularly limited. The amount of the Pack 1 primer reagent and the amount of the Pack 2 primer reagent contained in the primer reagent of the present invention are not particularly limited.

The four types of F primers and the two types of R primers contained in the Pack 2 primer reagent may form the following primer sets, for example. By using any one of the following primer sets, it is possible to amplify one type of the variant alone. Also, it is possible to amplify, for example, two, three, or four types of the variants by combining the following primer sets as appropriate depending on the variants to be detected. As a specific example, when V8a and V8b are to be amplified, the reagent may comprise the combination of the following primer set for V8a and the following primer set for V8b, for example. In this case, because both the primer sets have the same R primer, this combination includes two types of F primers and one type of R primer. The invention extends to a primer reagent comprising the Pack 1 primers as well as one or more of the following Primer sets for V8a, V8b, V4 and/or V4'.

Primer set for V8a
   the F primer (F_V8a)
   the R primer (R_V8a/b)
Primer set for V8b
   the F primer (F_V8b)
   the R primer (R_V8a/b)
Primer set for V4
   the F primer (F_V4)
   the R primer (R_V4/4')
Primer set for V4'
   the F primer (F_V4')
   the R primer (R_V4/4')

The Pack 3 primer reagent includes, for example:
the forward primer consisting of the oligonucleotide (F_V5a/b);
the forward primer consisting of the oligonucleotide (F_V7);
the forward primer consisting of the oligonucleotide (F_V9);
the reverse primer consisting of the oligonucleotide (R_V/multi); and
the reverse primer consisting of the oligonucleotide (R_V5b).

(F_V5a/b): the oligonucleotide consisting of the base sequence of SEQ ID NO: 13
(SEQ ID NO: 13)
5'-gtgaaaaaatcagtctcaagtaaag-3'

(F_V7): the oligonucleotide consisting of the base sequence of SEQ ID NO: 14
(SEQ ID NO: 14)
5'-gatctgaatsctgaaagagaaatag-3',
where s is g (guanine) or c (cytosine)

(F_V9): the oligonucleotide consisting of the base sequence of SEQ ID NO: 15
(SEQ ID NO: 15)
5'-tgtgatgcgctactcaatag-3'

(R_V/multi): the oligonucleotide consisting of the base sequence of SEQ ID NO: 5
(SEQ ID NO: 5)
5'-gctccatctgcatggc-3'

(R_V5b): the oligonucleotide consisting of the base sequence of SEQ ID NO: 16
(SEQ ID NO: 16)
5'-cctggatctccatatcctcc-3'

Variants of these oligonucleotides may also be used as described hereinbelow. Preferably, the primers consist of the oligonucleotides described herein.

The F primer (F_V5a/b) is a primer that anneals to exon 2 of the EML4 gene. The F primer (F_V7) is a primer that anneals to a region extending from the 25th base counted toward the upstream side from the fusion point at exon 14 of the EML4 gene to the 1st base counted toward the downstream side from the fusion point at exon 20 of the ALK gene. The F primer (F_V9) is a primer that anneals to a region extending from the 20th base counted toward the upstream side from the fusion point at exon 18 of the EML4 gene to the 1st base counted toward the downstream side from the fusion point at exon 20 of the ALK gene. The R primer (R_V/multi) is a primer that anneals to exon 20 of the ALK gene, as described above. The R primer (R_V5b) is a primer that anneals to an insertion region adjacent to the upstream of exon 20 of the ALK gene.

With the F primer (F_V5a/b) and the R primer (R_V/multi), a region including the fusion point of the EML4 gene and the ALK gene in the V5a may be amplified, and the length of the amplified fragment is, for example, about 70 bp including the regions of the respective primers. With the F primer (F_V5b) and the R primer (R_V5b), a region including the fusion point of the EML4 gene and the ALK gene in the V5b may be amplified, and the length of the amplified fragment is, for example, about 59 bp including the regions of the respective primers. With the F primer (F_V7) and the R primer (R_V/multi), a region including the fusion point of the EML4 gene and the ALK gene in the V7 may be amplified, and the length of the amplified fragment is, for example, about 58 bp including the regions of the respective primers. With the F primer (F_V9) and the R primer (R_V/multi), a region including the fusion point of the EML4 gene and the ALK gene in the V9 may be amplified, and the length of the amplified fragment is, for example, about 65 bp including the regions of the respective primers.

When the primer reagent of the present invention includes the Pack 3 primer reagent in addition to the Pack 1 primer reagent, not only the five types of variants (V1, V2, V3a, V3b, and V6) of the ALK fusion gene but also other four types of variants (V5a, V5b, V7, and V9) may be amplified at the same time in one reaction system including all these primers, for example. Thus, when the primer reagent of the present invention includes the Pack 1 primer reagent and the Pack 3 primer reagent, at least nine types of variants of the ALK fusion gene in total, including the major five types of variants, may be analyzed by checking whether or not the amplification occurred or the amount of amplification.

The amount of each of the three types of F primers and the two types of R primers contained in the Pack 3 primer reagent is not particularly limited. The ratio (molar ratio F:R) between the total molar amount (F) of the F primers and the total molar amount (R) of the R primers is, for example, 1:1 to 1:6. As a specific example, the ratio (molar ratio F:R) between them is 1:6. The total amount of the three types of F primers and the total amount of the two types of R primers contained in the Pack 3 primer reagent are not particularly limited. The amounts of the Pack 1 primer reagent and the Pack 3 primer reagent contained in the primer reagent of the present invention are not particularly limited.

The three types of F primers and the two types of R primers contained in the Pack 3 primer reagent may form the following primer sets, for example. By using any one of the following primer sets, it is possible to amplify one type of the variant alone. Also, it is possible to amplify, for example, two, three, or four types of the variants by combining the following primer sets as appropriate depending on the variants to be detected. As a specific example, when V5a and V5b are to be amplified, the reagent may comprise the combination of the following primer set for V5a and the following primer set for V5b, for example. In this case, because both the primer sets have the same F primer, this combination includes one type of F primer and two types of R primers. The invention extends to a primer reagent comprising the Pack 1 primers as well as one or more of the following Primer sets for V5a, V5b, V7 and/or V9 (as well as one or more of the Pack 2 Primer sets for V8a, V8b, V4 and/or V4').

Primer set for V5a
   the F primer (F_V5a/b)
   the R primer (R_V/multi)
Primer set for V5b
   the F primer (F_V5a/b)
   the R primer (R_V5b)
Primer set for V7
   the F primer (F_V7)
   the R primer (R_V/multi)
Primer set for V9
   the F primer (F_V9)
   the R primer (R_V/multi)

The Pack 4 primer reagent includes, for example,
the F primer consisting of the oligonucleotide (F_KIF/e24);
the F primer consisting of the oligonucleotide (F_KIF/e15);
the F primer consisting of the oligonucleotide (F_KIF/e17);
the F primer consisting of the oligonucleotide (F_KLC1);
the F primer consisting of the oligonucleotide (F_TFG); and
the R primer consisting of the oligonucleotide (R_V/multi).

(F_KIF/e24): the oligonucleotide consisting of the base sequence of SEQ ID NO: 17
   (SEQ ID NO: 17)
5'-ggcattctgcacagattg-3'

(F_KIF/e15): the oligonucleotide consisting of the base sequence of SEQ ID NO: 18
   (SEQ ID NO: 18)
5'-agaaataggaattgctgtggg-3'

(F_KIF/e17): the oligonucleotide consisting of the base sequence of SEQ ID NO: 19

(SEQ ID NO: 19)
5'-ccagcttcgagcacaag-3'

(F_KLC1): the oligonucleotide consisting of the base sequence of SEQ ID NO: 20
   (SEQ ID NO: 20)
5'-gggagtttggttctgtagatg-3'

(F_TFG): the oligonucleotide consisting of the base sequence of SEQ ID NO: 21
   (SEQ ID NO: 21)
5'-ttccaccaatattcctgaaaatg-3'

(R_V/multi): the oligonucleotide consisting of the base sequence of SEQ ID NO: 5
   (SEQ ID NO: 5)
5'-gctccatctgcatggc-3'

Variants of these oligonucleotides may also be used as described hereinbelow. Preferably, the primers consist of the oligonucleotides described herein.

The F primer (F_KIF/e24) is a primer that anneals to exon 24 of the KIF5B gene. The F primer (F_KIF/e15) is a primer that anneals to exon 15 of the KIF5B gene. The F primer (F_KIF/e17) is a primer that anneals to exon 17 of the KIF5B gene. The F primer (F_KLC1) is a primer that anneals to exon 9 of the KLC1 gene. The F primer (F_TFG) is a primer that anneals to exon 3 of the TFG gene. The R primer (R_V/multi) is a primer that anneals to exon 20 of the ALK gene, as described above.

With the F primer (F_KIF/e24) and the R primer (R_V/multi), a region including the fusion point of the KIF5B gene and the ALK gene in the KIF5B exon24-ALK may be amplified, and the length of the amplified fragment is, for example, about 63 bp including the regions of the respective primers. With the F primer (F_KIF/e15) and the R primer (R_V/multi), a region including the fusion point of the KIF5B gene and the ALK gene in the KIF5B exon15-ALK may be amplified, and the length of the amplified fragment is, for example, about 68 bp including the regions of the respective primers. With the F primer (F_KIF/e17) and the R primer (R_V/multi), a region including the fusion point of KIF5B and the ALK gene in the KIF5B exon17-ALK may be amplified, and the length of the amplified fragment is, for example, about 62 bp including the regions of the respective primers. With the F primer (F_KLC1) and the R primer (R_V/multi), a region including the fusion point of the KLC1 gene and the ALK gene in the KLC1-ALK may be amplified, and the length of the amplified fragment is, for example, about 66 bp including the regions of the respective primers. With the F primer (F_TFG) and the R primer (R_V/multi), a region including the fusion point of the TFG gene and the ALK gene in the TFG-ALK may be amplified, and the length of the amplified fragment is, for example, about 68 bp including the regions of the respective primers.

When the primer reagent of the present invention includes the Pack 4 primer reagent in addition to the Pack 1 primer reagent, not only the five types of variants (V1, V2, V3a, V3b, and V6) of the ALK fusion gene but also other five types of variants (KIF5B-ALK exon24, KIF5B-ALK exon15, KIF5B-ALK exon17, KLC1-ALK and TFG-ALK) of the ALK fusion gene may be amplified at the same time in one reaction system including all these primers, for example. Thus, when the primer reagent of the present invention includes the Pack 1 primer reagent and the Pack 4 primer reagent, at least 10 types of variants of the ALK fusion gene in total, including the major five types of variants, may be analyzed and detected by checking whether or not the amplification occurred or the amount of amplification.

The amount of each of the five types of F primers and the one type of R primer contained in the Pack 4 primer reagent is not particularly limited. The ratio (molar ratio F:R) between the total molar amount (F) of the F primers and the total molar amount (R) of the R primer is, for example, 1:1 to 1:6. As a specific example, the ratio (molar ratio F:R) between them is 1:6. The total amount of the five types of F primers contained in the Pack 4 primer reagent is not particularly limited. The amounts of the Pack 1 primer reagent and the Pack 4 primer reagent contained in the primer reagent of the present invention are not particularly limited.

The five types of F primers and the one type of R primer contained in the Pack 4 primer reagent may form the following primer sets, for example. By using any one of the following primer sets, it is possible to amplify one type of the variant alone. Also, for example, two, three, four, or five types of variants may be amplified by combining the following primer sets depending on the variants to be detected. As a specific example, when the KIF5B-ALK exon24 and the KIF5B-ALK exon15 are to be amplified, the reagent may comprise the combination of the following primer set for KIF5B-ALK exon 24 and the following primer set for KIF5B-ALK exon 15, for example. In this case, because both the primer sets have the same R primer, this combination includes two types of F primers and one type of R primer. The invention extends to a primer reagent comprising the Pack 1 primers as well as one or more of the following Primer sets for KIF5B exon24-ALK, KIF5B exon15-ALK, KIF5B exon17-ALK, KLC1-ALK and/or TFG-ALK (as well as one or more of the Pack 2 Primer sets for V8a, V8b, V4 and/or V4' and/or one or more of the Pack 3 Primer sets for V5a, V5b, V7 and/or V9).

Primer set for KIF5B exon24-ALK
   the F primer (F_KIF/e24)
   the R primer (R_V/multi)
Primer set for KIF5B exon15-ALK
   the F primer (F_KIF/e15)
   the R primer (R_V/multi)
Primer set for KIF5B exon17-ALK
   the F primer (F_KIF/e17)
   the R primer (R_V/multi)
Primer set for KLC1-ALK
   the F primer (F_KLC1)
   the R primer (R_V/multi)
Primer set for TFG-ALK
   the F primer (F_TFG)
   the R primer (R_V/multi)

The primer reagent of the present invention may comprise only the Pack 1 primer reagent as primers as described above. Alternatively, in addition to the Pack 1 primer reagent, the primer reagent of the present invention further may comprise one type, two types, or all the three types of primer reagents selected from the Pack 2 primer reagent, the Pack 3 primer reagent, and the Pack 4 primer reagent, for example. Examples of the combination of the Pack primer reagents in the primer reagent of the present invention include the combinations 1 to 8 shown below.
1. Pack 1 primer reagent
2. Pack 1 primer reagent/Pack 2 primer reagent
3. Pack 1 primer reagent/Pack 3 primer reagent
4. Pack 1 primer reagent/Pack 4 primer reagent
5. Pack 1 primer reagent/Pack 2 primer reagent/Pack 3 primer reagent
6. Pack 1 primer reagent/Pack 2 primer reagent/Pack 4 primer reagent
7. Pack 1 primer reagent/Pack 3 primer reagent/Pack 4 primer reagent
8. Pack 1 primer reagent/Pack 2 primer reagent/Pack 3 primer reagent/Pack 4 primer reagent When the primer reagent of the present invention includes any of the combinations 2 to 8, the Pack 1 primer reagent and the other primer reagent(s) may be used at the same time in one reaction system (single reagent system), or may be used independently in separate reaction systems (multiple-reagent system), for example. In the case of the former single reagent system, the primer reagent of the present invention may be configured so that, for example, all the primers are mixed together. In this case, a primer common among two or more of the Pack primer reagents may be contained in the respective Pack primer reagents, or may be shared among the respective Pack primer reagents, for example. In the case of the latter multiple-reagent system, the primer reagent of the present invention may be configured so that, for example, each Pack primer reagent is provided independently so as to form a single reagent system.

In the primer reagent of the present invention, each of the above-described primers comprises the following oligonucleotides, for example.

Specifically, each of the primers comprises, for example, an oligonucleotide consisting of a base sequence that is obtained by deletion, substitution, insertion, and/or addition of one or a few bases in the base sequence of the above sequence identification number and anneals to substantially the same region as the annealing region of the oligonucleotide consisting of the base sequence of the above sequence identification number. The "one or a few" means 1 to 5, 1 to 4, 1 to 3, or 1 or 2, for example. The meaning of "annealing to substantially the same region (and grammatical variations thereof)" encompasses, for example, in addition to annealing to the same region as the annealing region, annealing to a region shorter than the annealing region by a few bases on at least one of the 5' side and the 3' side thereof and annealing to a region longer than the annealing region by a few bases on at least one of the 5' side and the 3' side thereof (the same applies hereinafter). The "few bases" means 1 to 5 bases, 1 to 4 bases, 1 to 3 bases, or 1 or 2 bases, for example.

Furthermore, each of the primers comprises, for example, an oligonucleotide that has a base sequence with a predetermined identity to the oligonucleotide consisting of the base sequence of the above sequence identification number and anneals to substantially the same region as the annealing region of the oligonucleotide consisting of the base sequence of the above sequence identification number. The predetermined identity is, for example, at least 80%, at least 85%, at least 90%, at least 95%, at least 96%, at least 97%, at least 98%, or at least 99%. The identity may be calculated with analysis software such as BLAST or FASTA using default parameters, for example (the same applies hereinafter).

Examples of the building block of the oligonucleotide constituting the primer include nucleotide residues and artificial nucleic acid residues. Examples of the nucleotide include deoxyribonucleotides and ribonucleotides. The nucleotide may be unmodified nucleotide or modified nucleotide, for example. Examples of the artificial nucleic acid include: PNAs (Peptide Nucleic Acids); LNAs (Locked Nucleic Acids), which are RNA analogs; BNAs (Bridged Nucleic Acids); and ENA (2'-O, 4'-C-Ethylenebridged Nucleic Acid). The primers in the present invention each consist of, for example, an oligonucleotide (DNA) including or consisting of deoxyribonucleotide residues.

The primer reagent of the present invention further may contain, for example, a solvent(s) and any other component used for the amplification reaction, a reverse transcription reaction, and the like. Regarding the other component, examples of the other component to be described below may be referred to, for example.

(2) Amplification Reagent Kit

As described above, the amplification reagent kit of the present invention is an amplification reagent kit for an ALK fusion gene, including the primer reagent according to the present invention. The amplification reagent kit of the present invention is characterized in that it includes the primer reagent of the present invention, and other configurations and conditions are not particularly limited. According to the amplification reagent kit of the present invention, the plurality of variants of the ALK fusion gene may be amplified at the same time in the same reaction system, for example. The descriptions regarding the primer reagent of the present invention may be applied to the amplification reagent kit of the present invention, unless otherwise noted.

The amplification reagent kit of the present invention may include only the Pack 1 primer reagent as primers, or it further may include other primers. As described above, examples of the other primers include the Pack 2 primer reagent, the Pack 3 primer reagent, and the Pack 4 primer reagent (or primer sets thereof). As a specific example, the amplification reagent kit of the present invention may include one type, two types, or all the three types of them, in addition to the Pack 1 primer reagent.

The amplification reagent kit of the present invention may be configured so that the F primers and the R primers in the Pack 1 primer reagent are all contained in the same reaction system when they are in use.

When the amplification reagent kit of the present invention further includes at least one selected from the group consisting of the Pack 2 primer reagent, the Pack 3 primer reagent, and the Pack 4 primer reagent, the amplification reagent kit may be configured so that the F primers and the R primers in the Pack 1 primer reagent and the F primers and the R primers in the other Pack primer reagent(s) are all contained in the same reaction system they are in use.

The amplification reagent kit of the present invention also may be configured so that, for example, the F primers and the R primers in each of the Pack primer reagents are all contained in the same reaction system when they are in use. That is, the Pack 1 primer reagent and the other Pack primer reagent(s) may form different reagent systems, respectively. In this case, amplification reactions may be carried out separately by providing different reaction systems using the respective Pack primer reagents. In the configuration of the amplification reagent kit of the present invention in which the different reagent systems are used, all the reagents may be contained in the same container with the respective reagents being isolated from each other, or they may be contained in different containers, for example.

The amplification reagent kit of the present invention further may include, for example, a solvent(s) and any other component used for the amplification reaction, a reverse transcription reaction, and the like. Regarding the other component, examples of the other component to be described below may be referred to, for example. In some embodiments, the amplification reagent kit may comprise the primer reagent described herein, a polymerase, deoxynucleoside triphosphates (dNTP), albumin, and/or a buffer solution. In one aspect, the polymerase may be a RNA or DNA polymerase. In another aspect, the amplification reagent kit may further comprise RNase inhibitor, a reserve transcriptase, and/or a reducing agent. Also, the amplification reagent kit of the present invention further may include instructions for use.

(3) Amplification Method

As described above, the amplification method according to the present invention is an amplification method for amplifying an ALK fusion gene, including the step of: amplifying a template nucleic acid in one reaction system including the primer reagent for an ALK fusion gene (or amplification reagent kit) according to the present invention. The amplification method of the present invention is characterized in that the primer reagent (or amplification reagent kit) of the present invention is used therein, and other conditions and steps are not particularly limited. The description regarding the primer reagent of the present invention may be applied to the amplification method of the present invention, unless otherwise noted.

In the amplification step, there is no particular limitation on the amplification method of a template nucleic acid as long as the method uses a primer. Examples of the amplification method include PCR (Polymerase Chain Reaction), NASBA (Nucleic Acid Sequence Based Amplification), TMA (Transcription-Mediated Amplification), and SDA (Strand Displacement Amplification). In the present invention, the primer reagent of the present invention is used as a primer in the amplification step.

The conditions of the amplification method are not particularly limited. For example, general conditions may be employed. In the case where the amplification method is PCR, for example, the following steps are repeated: (1) dissociation of a double-stranded DNA template nucleic acid into a single-stranded DNA, (2) annealing of a primer to the single-stranded DNA, and (3) extension of the primer. In the PCR, with the three steps (1) to (3) being considered as one cycle, the number of cycles is not particularly limited. The lower limit is, for example, 20 cycles, 25 cycles, or 30 cycles, and the upper limit is, for example, 100 cycles, 70 cycles, or 50 cycles. The number of cycles is, for example, in the range from 30 to 100 cycles, 30 to 70 cycles, or 30 to 50 cycles. The conditions of the respective steps are not particularly limited and are, for example, as follows. (1) The dissociation step is performed, for example, at the temperature from 90° C. to 99° C. for 1 to 120 seconds and at the temperature from 92° C. to 95° C. for 1 to 60 seconds, (2) the annealing step is performed, for example, at the temperature from 40° C. to 70° C. for 1 to 300 seconds and at the temperature from 50° C. to 70° C. for 5 to 60 seconds, and (3) the extension step is performed, for example, at the temperature from 50° C. to 80° C. for 1 to 300 seconds and at the temperature from 50° C. to 75° C. for 5 to 60 seconds. In some embodiments, the amplification method may comprise providing a reaction mixture comprising a double-stranded target nucleotide and the amplification reagent kit described herein; heating the reaction mixture to a first predetermined temperature for a first predetermined time to separate the strands of the target nucleotide from each other; cooling the reaction mixture to a second predetermined temperature for a second predetermined time under conditions to allow the forward and reverse primers to hybridize with their complementary sequences on the strands of the target nucleotide, and to allow the polymerase to extend the forward and reverse primers; and repeating the heating and cooling at least 10, 20, 30, 40, 50, 100, or 150 times.

In the amplification step, the reaction system is, for example, a reaction solution. The volume of the reaction system is not particularly limited and is, for example, from 1 to 500 µL or from 1 to 100 µL. The reaction system includes, for example, the primer reagent of the present invention and the template nucleic acid, and further includes a solvent and other components used for amplification reaction. Examples of the solvent include water and buffer solutions such as Tris-HCl, Tricine, MES, MOPS, HEPES, and CAPS. Specific examples thereof include commercially available PCR buffer solutions and buffer solutions included in commercially available PCR kits. Examples of the other components include polymerase, nucleotide triphosphate, heparin, betaine, KCl, $MgCl_2$, $MgSO_4$, glycerol, and albumin. Examples of the albumin include bovine serum albumin (BSA), human serum albumin, rat serum albumin, and horse serum albumin. When the amplification method of the present invention includes a reverse transcription step to be described below, the reaction system may contain, as other components, an RNase inhibitor, a reverse transcriptase such as RNA-dependent DNA polymerase, a reducing agent, and the like. Examples of the RNase inhibitor include RNase Inhibitor Recombinant type (trade name, TOYOBO). Examples of the reverse transcriptase include SuperScriptIII (trade name, Invitrogen) and ReverTra Ace (trade name, TOYOBO). Examples of the reducing agent include DTT. In the reaction system, the proportions and the order of addition of the respective components are not particularly limited.

The polymerase is not particularly limited, and common DNA polymerase may be used, for example. The polymerase may be, for example, a non-human-derived polymerase, and specific examples thereof include polymerases derived from heat-resistant bacteria. Specific examples of the polymerase include GeneTaq (product name, NIPPON GENE CO., LTD.), PrimeSTAR Max DNA Polymerase (product name, TAKARA BIO INC), *Thermus aquaticus*-derived DNA polymerases (U.S. Pat. Nos. 4,889,818 and 5,079,352) (trade name: Taq polymerase), *Thermus thermophilus*-derived DNA polymerase (WO 91/09950) (rTth DNA polymerase), *Pyrococcus furiosus*-derived DNA polymerase (WO 92/9689) (Pfu DNA polymerase: Stratagenes), and *Thermococcus litoralis*-derived DNA polymerase (EP 0455430 (trademark: Vent), New England Biolabs). In the reaction system, the amount of the polymerase to be added is not particularly limited. As a specific example, the lower limit is, for example, 0.001, 0.005, 0.01, 0.05, 0.1, 1, or 5 U and the upper limit is, for example, 50, 80, 100, or 150 U, i.e., the amount of the polymerase to be added is, for example, in the range from 0.001 to 150 U or 0.01 to 100 U per reaction system (50 μL). With respect to the unit of activity (U) of the polymerase, generally, 1 U denotes the activity that allows all 10 nmol of nucleotide to be taken into an acid-insoluble precipitate in 30 minutes at 74° C. in a reaction solution for activity measurement, with an activated salmon sperm DNA being used as a template primer. The composition of the reaction solution is, for example, as follows: 25 mmol/L TAPS buffer solution (pH 9.3, 25° C.), 50 mmol/L KCl, 2 mmol/L $MgCl_2$, 1 mmol/L mercapto ethanol, 200 μmol/L dATP, 200 μmol/L dGTP, 200 μmol/L dTTP, 100 μmol/L "$\alpha$-$^{32}$P" dCTP, and 0.25 mg/mL activated salmon sperm DNA.

Examples of the nucleotide triphosphate generally include dNTPs (dATP, dCTP, dGTP, and dTTP and dUTP). In the reaction system, the amount of the nucleotide triphosphate to be added is not particularly limited. As a specific example, the lower limit is, for example, 0.01 mmol/L, 0.05 mmol/L, or 0.1 mmol/L and the upper limit is, for example, 1 mmol/L, 0.5 mmol/L, or 0.3 mmol/L, i.e., the amount of the nucleotide triphosphate to be added is, for example, in the range from 0.01 to 1 mmol/L, from 0.05 to 0.5 mmol/L, or from 0.1 to 0.3 mmol/L.

The template nucleic acid to be used in the amplification step (which contains the ALK fusion gene), is, for example, DNA. The DNA is, for example, a nucleic acid of biological origin. The DNA of biological origin may be, for example, DNA contained in a biological sample or cDNA prepared by reverse transcription from RNA contained in a biological sample. Examples of RNA contained in a biological sample include total RNA and mRNA. The template nucleic acid may be the one that may include the ALK fusion gene, for example.

Examples of the biological sample include blood (for example, whole blood, blood cells such as leukocyte, blood plasma, blood serum, and the like), tissues (for example, the large intestine, the lung, and the like), oral tissues (for example, oral mucosa, and the like), somatic cells (for example, nail, hair, and the like), germ cells, expectoration, amniotic fluid, peritoneal fluid, urine, and gastric juice. Other examples of the biological sample include samples of biological origin, such as a fluid obtained by gastric lavage, paraffin-embedded tissues, and cultured cells. For example, nucleic acids (for example, DNA and RNA) contained in biological samples may be isolated from cells contained in the biological samples. As a method for isolation, a common method may be employed, for example. Preferably, the sample is from a human.

In the amplification step, the template nucleic acid may be added to a reaction system as a test sample including the template nucleic acid.

As the test sample, for example, the biological sample may be used as it is. Also, a diluted solution obtained by dissolving, suspending, or mixing the biological sample to a solvent may be used or the biological sample pretreated may be used. There is no particular limitation on the pretreatment, and examples thereof include a treatment of releasing nucleic acids from cells contained in the biological sample. In the case where the biological sample is blood, a specific example of the biological sample pretreated is a hemolysis sample obtained by applying hemolysis treatment to blood as pretreatment. The hemolysis sample may be prepared by diluting whole blood with a solvent, for example. Examples of the solvent include water and buffer solutions. The dilution ratio (volume) of whole blood is not particularly limited, and is, for example, from 100:1 to 2000:1 or from 200:1 to 1000:1.

The amount of the template nucleic acid in the reaction system is not particularly limited.

The amount of the primer reagent of the present invention in the reaction system is not particularly limited. As a specific example, the amounts of a F primer and a R primer corresponding to a specific variant are, for example, from 0.1 to 4 μmol/L and 0.25 to 1.5 μmol/L per reaction system (50 μL), respectively. In other words, in the case of the Pack 1 primer reagent, the amounts of the F primers (F_V1), (F_V2), (F_V3a), (F_V3b), and (F_V6) are each, for example, the aforementioned amount per reaction system (50 μL), the amount of the R primer (R_V/multi) is, for example, four times the aforementioned amount per reaction system (50 μL) because the R primer (R_V/multi) is common among four types of variants, and the amount of the R primer (R_V6) is, for example, the aforementioned amount per reaction system (50 μL). The ratio between the F primer and the R primer in the reaction system is not particularly limited, and examples of the ratio include the molar ratios described for the primer reagent of the present invention.

As described above, besides the Pack 1 primer reagent, the primer reagent of the present invention may comprise at least one primer reagent selected from the group consisting of the Pack 2 primer reagent, the Pack 3 primer reagent, and the Pack 4 primer reagent (or primer sets thereof). As for the Pack primers other than the Pack 1 primer reagent, the amounts of the respective F primers and the R primers are not particularly limited and are, for example, the same amounts as those in the Pack 1 primer reagent.

In the case where the Pack 1 primer reagent and other Pack primer reagent(s) are mixed in the same reaction system, the target ALK fusion gene variants of the respective Pack primer reagents may be amplified by performing an amplification reaction for one reaction system, for example. In the case where the Pack 1 primer reagent and other Pack primer reagents are individually added to separate reaction systems, target ALK fusion gene variants of the respective Pack primer reagents may be amplified in the respective reaction systems by performing an amplification reaction for each of the respective reaction systems, for example.

As described above, in the case where a template nucleic acid of the amplification reaction in the amplification step is cDNA, the amplification method of the present invention may further include a reverse transcription step of preparing cDNA by reverse transcription from RNA, for example. In this case, for example, RNA is a template nucleic acid (Rt) of the reverse transcription in the reverse transcription step, and cDNA obtained in the reverse transcription step is a template nucleic acid (Am) of the amplification reaction in the amplification step. As described above, the RNA may be RNA contained in a biological sample, for example.

The reverse transcription step and the amplification step may be performed in separate reaction systems or in the same reaction system, for example. In the former case, reverse transcription may be performed by using a reaction system including a template nucleic acid (Rt) of the reverse transcription and a reverse transcription primer selected freely. Thereafter, an amplification reaction may be performed, with the reaction system of the reverse transcription being used as a test sample including a template nucleic acid (Am) of the amplification reaction, by using a new reaction system including the test sample and the primer reagent of the present invention, for example. In the latter case, the reverse transcription and the amplification reaction may be performed by using a reaction system including a template nucleic acid (Rt) of the reverse transcription, a reverse transcription primer, and the primer reagent of the present invention, for example. In this case, for example, in the reaction system, cDNA is prepared by reverse transcription on the basis of a template nucleic acid (Rt), and an amplification reaction is performed with the thus-prepared cDNA used as a template nucleic acid (Am) of the amplification reaction.

The reaction system in the reverse transcription step includes, for example, the freely-selected reverse transcription primer and the template nucleic acid (Rt), and further includes a solvent and other components used for reverse transcription. Examples of the solvent include those described for the amplification step. Examples of the other components include: reverse transcriptases such as RNA-dependent DNA polymerase; the aforementioned nucleotide triphosphates; the aforementioned RNase inhibitors; and reducing agents. In the reaction system, the proportions and the order of addition of the respective components are not particularly limited.

In the reaction system of the reverse transcription step, the amount of the template nucleic acid (Rt) of the reverse transcription is not particularly limited.

As described above, according to the amplification method of the present invention, at least five types of major variants highly relevant to lung cancer among ALK fusion genes may be amplified in one reaction system. Therefore, by checking whether or not an amplification product is produced by the amplification reaction using the primer reagent of the present invention, the presence or absence of any of the five types of variants may be analyzed, detected, or qualified. Thus, the amplification method of the present invention may include the step of amplifying a template nucleic acid in a test sample and further, the step of detecting an ALK fusion gene in the test sample by detecting amplification of the template nucleic acid, for example. The analysis of an ALK fusion gene by the detection of the amplification will be described in the context of the analysis method of the present invention to be described below.

(4) Analysis Method

As described above, the analysis method according to the preset invention is an analysis method for analyzing an ALK fusion gene, including the steps of: amplifying a template nucleic acid in a test sample by the amplification method for an ALK fusion gene according to the present invention; and detecting an ALK fusion gene in the test sample by detecting amplification of the template nucleic acid. The present invention also provides a method for detecting the presence of an ALK fusion gene, including the steps of: amplifying a template nucleic acid in a test sample by the amplification method according to the present invention; and detecting an ALK fusion gene in the test sample by detecting amplification of the template nucleic acid. The present invention is characterized in that an ALK fusion gene is amplified using the primer reagent of the present invention, and other conditions and steps are not particularly limited. The descriptions regarding the primer reagent and the amplification method of the present invention may be applied to the analysis method of the present invention, unless otherwise noted.

In the analysis method of the present invention, the description regarding the amplification method of the present invention may be applied to the amplification step, for example.

In the detection step, the detection of amplification of the template nucleic acid may be the detection of the presence or absence of an amplification product or the detection of the amount of the amplification product, for example. For example, the former case may be referred to as qualitative analysis and the latter case may be referred to as quantitative analysis.

In the detection step, the detection method of the amplification of a template nucleic acid is not particularly limited, and a common method may be employed. Examples of the detection method of the amplification include a detection method using a probe and a detection method using an intercalator.

First, in some embodiments, the former method using a probe is a method in which a probe hybridizable to a target amplification product (hereinafter, also referred to as the "test nucleic acid") is used. According to this method, for example, the amplification product may be detected on the basis of whether or not the probe is hybridized to the amplification product or the amount of the probe hybridized to the amplification product.

The sequence of the probe is not particularly limited and may be set as a sequence complementary to a region to be amplified by the primer reagent of the present invention, for example. The sequence of the probe may be complementary to the sense strand of an ALK fusion gene or may be complementary to the antisense strand of an ALK fusion gene, for example. In the case where the template nucleic acid is cDNA of an ALK fusion gene, the sequence of the probe may be a sequence complementary to the cDNA or may be a sequence that is in the same direction as the cDNA.

The probe includes an oligonucleotide as a nucleic acid, for example. Examples of the building block of the oligonucleotide include nucleotide residues and artificial nucleic acid residues, and the description regarding the building block of the primer may be applied. The probe in the present invention according to some embodiments is a probe of an oligonucleotide (DNA) including or consisting of deoxyribonucleotide residues.

The length of the probe is not particularly limited, and the lower limit is, for example, 5-mer or 10-mer and the upper limit is, for example, 50-mer or 30-mer, i.e., the length of the probe is, for example, in the range from 5-mer to 50-mer or from 10-mer to 30-mer.

The probe may include a labeling substance (or a label) in addition to the oligonucleotide, for example. In this case, examples of the probe include a labeled probe in which the oligonucleotide is labeled (modified or attached) with the labeling substance. In one aspect, the labeling substance is not part of a naturally occurring oligonucleotide sequence, and thus the labeled oligonucleotide as a whole is not a naturally occurring oligonucleotide sequence. In another aspect, the labeling substance does not include any particular nucleotide, such as tyrosine. In another aspect, the labeling substance is a synthetic material not existing in nature.

In the labeled probe, there is no particular limitation on the site of the oligonucleotide labeled with the labeling substance. Specifically, the site may be, for example, a 5' end region of the oligonucleotide, a 3' end region of the oligonucleotide, or both the 5' end region and the 3' end region of the oligonucleotide. The 5' end region is, for example, a region of the 1st to 5th bases from the 5' end of the oligonucleotide. Any of the 1st, 2nd, 3rd, 4th, and 5th bases may be labeled. As a specific example, the 1st base (the 5' end base) is labeled. The 3' end region is, for example, a region of the 1st to 5th bases from the 3' end of the oligonucleotide. Any of the 1st, 2nd, 3rd, 4th, and 5th bases may be labeled. As a specific example, the 1st base (the 3' end base) is labeled.

The method of labeling with the labeling substance is not particularly limited. For example, a base in the oligonucleotide may be labeled directly or the base in the oligonucleotide may be labeled indirectly. In the latter case, for example, the base may be labeled indirectly by labeling any site of a nucleotide residue including the base.

Examples of the labeling substance include fluorescent materials such as fluorophore. Examples of the fluorescent materials include fluorescein, phosphor, rhodamine, and polymethine dye derivatives. Examples of commercially available fluorescent materials include Pacific Blue (trademark, Molecular Probes), BODIPY FL (trademark, Molecular Probes), FluorePrime (product name, Amersham Pharmacia), Fluoredite (product name, Millipore Corporation), FAM (trademark, ABI CO LTD.), Cy3 and Cy5 (product names, Amersham Pharmacia), and TAMRA (trademark, Molecular Probes). Conditions for fluorescent material detection are not particularly limited and may be determined appropriately according to the type of a fluorescent material to be used, for example. As a specific example, Pacific Blue may be detected, for example, at a detection wavelength from 450 to 480 nm, TAMRA may be detected, for example, at a detection wavelength from 585 to 700 nm, and BODIPY FL may be detected, for example, at a detection wavelength from 515 to 555 nm.

The labeled probe may be the one that exhibits a signal originating in the labeling substance depending on whether it is alone or it forms a hybrid. The type of the signal is not particularly limited, and examples thereof include fluorescence and coloring. Examples of the coloring include color development and color change. In the case where the signal is fluorescence, the signal value is, for example, fluorescence intensity. In the case where the signal is coloring, examples of the signal value include reflectance, absorbance, and transmittance. The signal may be exhibited directly or indirectly from the labeling substance, for example. According to such a labeled probe, for example, whether the probe is alone or forms a hybrid by the detection of the signal may be analyzed, whereby the amplification may be analyzed, detected, and quantified.

Examples of the labeled probe include a labeled probe that exhibits a signal when it is alone (not hybridized to another molecule) and does not exhibit a signal when it forms a hybrid and a labeled probe that does not exhibit a signal when it is alone and exhibits a signal when it forms a hybrid. In the case where the labeling substance is a fluorescent material, examples of the labeled probe include a probe that is labeled with the fluorescent material, exhibits fluorescence when it is alone, and allows fluorescence to be reduced (for example, quenched) when it forms a hybrid. Such a phenomenon generally is called a fluorescence quenching phenomenon, and a probe that utilizes such a phenomenon generally is called a fluorescence quenching probe. According to such a fluorescence quenching probe, for example, the hybridization of the probe to the hybridization region and the dissociation of the probe from the hybridization region may be checked based on the change in signal intensity of the fluorescent material (for example, change in fluorescence intensity).

In the case where the labeled probe is a so-called fluorescence quenching probe, the probe may include a cytosine base complementary to a guanine base at a hybridization region of the test nucleic acid to be hybridized with the probe in at least one of the 5' end region and the 3' end region, for example. Specifically, for example, the 5' end base or the 3' end base is a cytosine base. In the labeled probe in accordance with some embodiments, the cytosine base is labeled with the fluorescent material, for example. Such a labeled probe generally is called a guanine quenching probe among fluorescence quenching probes and is known as a so-called QProbe (registered trademark). When the guanine quenching probe hybridizes to the test nucleic acid, the cytosine base of the probe approaches the guanine base in the hybridization region, and the fluorescence of the fluorescent material decreases i.e. the fluorescence intensity decreases. Therefore, according to the guanine quenching probe, for example, the hybridization of the probe to the hybridization region and the dissociation of the probe from the hybridization region may be checked based on the change in signal intensity of the fluorescent material (for example, change in fluorescence intensity).

The probe may comprise a phosphate group added to the 3' end thereof, for example. As will be described below, the amplification step using the primer reagent and the detection step using the probe may be performed in the same reaction system including the primer reagent and the probe, for example. In this case, by using the probe including a phosphate group added to the 3' end thereof, for example, the extension of the probe itself may be sufficiently prevented in the amplification step. The same effect may be obtained by adding the labeling substance to the 3' end of the probe, for example.

In the detection step, probes for the respective variants may be used or a probe(s) common to two or more types of variants may be used, for example. In the case where one type of probe is used, the detection step may be performed in a reaction system including the one type of probe, for example. In the case where two or more types of probes are used, the detection step may be performed using separate reaction systems for the respective probes or using a reaction system including all the probes, for example.

In the case where more than one labeled probe is used as the probe, labeling substances for the respective labeled probes may be the same or different, for example. In the latter case, for example, the labeling substances are different labeling substances to be detected under different conditions. Specific examples of such labeling substances include different labeling substances to be detected at different detection wavelengths. When the different labeling substances are used, for example, it is possible to detect amplification products of the respective variants separately by changing the detection condition even in the same reaction system.

The specific examples of the probe will be described below. However, the present invention is not limited to these examples.

A probe set (hereinafter, Pack 1 probe reagent) for V1, V2, V3a, V3b, and V6 to be amplified by the Pack 1 primer reagent is as shown below, for example. P1-1 is a probe that detects V1, V2, V3a, and V3b. P1-2 is a probe that detects V6. The respective probes in the Pack 1 probe reagent may be used alone, for example.

```
P1-1: an oligonucleotide consisting of a base
sequence of SEQ ID NO: 22
                                        (SEQ ID NO: 22)
5'-caccaggagctgca-3'

P1-2: an oligonucleotide consisting of a base
sequence of SEQ ID NO: 23
                                        (SEQ ID NO: 23)
5'-cctgtgtagtgcttcaa-3'
```

A probe set (hereinafter, Pack 2 probe reagent) for V8a, V8b, V4, and V4' to be amplified by the Pack 2 primer reagent is as shown below, for example. P2-1 is a probe that detects V4 and V4'. P2-2 is a probe that detects V8a and V8b. The respective probes in the Pack 2 probe reagent may be used alone, for example. The Pack 2 probe reagent may be used independently from the Pack 1 probe reagent, for example.

P2-1: an oligonucleotide consisting of a base sequence of SEQ ID NO: 24 (SEQ ID NO: 24) 5'-agctccgcacctc-3'
P2-2: an oligonucleotide consisting of a base sequence of SEQ ID NO: 25 (SEQ ID NO: 25) 5'-ccatgttgcagctga-3'

A probe set (hereinafter, Pack 3 probe reagent) for V5a, V5b, V7, and V9 to be amplified by the Pack 3 primer reagent is as shown below, for example. P3-1 is a probe that detects V5a, V7, and V9. P3-2 is a probe that detects V5b. The respective probes in the Pack 3 probe reagent may be used alone, for example. The Pack 3 probe reagent may be used independently from the Pack 1 probe reagent, for example.

```
P3-1: an oligonucleotide consisting of a base
sequence of SEQ ID NO: 26
                                        (SEQ ID NO: 26)
5'-caccaggagctgca-3'
```

```
P3-2: an oligonucleotide consisting of a base
sequence of SEQ ID NO: 27
                                        (SEQ ID NO: 27)
5'-agtaaaggttcagagctc-3'
```

A probe set (hereinafter, Pack 4 probe reagent) for KIF5B exon24-ALK, KIF5B exon15-ALK, KIF5B exon17-ALK, KLC1-ALK, and TFG-ALK to be amplified by the Pack 4 primer reagent is as shown below, for example. P4-1 is a probe that detects KIF5B exon24-ALK, KIF5B exon15-ALK, KIF5B exon17-ALK, KLC1-ALK, and TFG-ALK. The Pack 4 probe reagent may be used independently from the Pack 1 probe reagent, for example.

```
P4-1: an oligonucleotide consisting of a base
sequence of SEQ ID NO: 28
                                        (SEQ ID NO: 28)
5'-caccaggagctgca-3'
```

The Pack 1 probe reagent, the Pack 2 probe reagent, the Pack 3 probe reagent, and the Pack 4 probe reagent may be labeled with labeling substances as described above, for example. A cytosine base at least one of the 5' end and the 3' end may be labeled, for example.

In the analysis method of the present invention, for example, the amplification step using the primer reagent (or amplification reagent kit) of the present invention and the detection step using the probe may be performed in separate reaction systems, respectively, or may be performed in the same reaction system. In the former case, for example, the amplification reaction may be performed in a reaction system including the primer reagent, and thereafter, using the amplification product obtained in the reaction system of the amplification reaction and the probe, a reaction system for the detection step may be newly prepared. Also, in the former case, the amplification reaction may be performed in a reaction system including the primer reagent, and the probe further may be added to the reaction system of the amplification reaction during or after the amplification reaction to perform the detection step. In the latter case, the amplification reaction may be performed in a reaction system including the primer reagent and the probe, and the detection step may be performed in the reaction system as it is. According to the latter method, for example, there is no need to expose the reaction system to an external environment during or after the amplification reaction in order to add the probe, and the amplification reaction and the detection step may be performed continuously.

In the reaction system of the detection step, the amount of the probe is not particularly limited. Specifically, with respect to the amount of one type of probe per 50 µL of the reaction system, the lower limit is, for example, 1 pmol and the upper limit is, for example, 100 µmol. In the reaction system, the concentration of the probe is, for example, from 10 to 1000 nmol/L or from 20 to 500 nmol/L.

In the case where the detection step is detection of the amplification using the probe, the detection may be performed by melting curve analysis.

Generally, the melting curve analysis also is referred to as "Tm analysis" that utilizes a melting temperature (Tm) at which a double-stranded nucleic acid is dissociated. For example, when a solution including a double-stranded nucleic acid such as double-stranded DNA is heated, the absorbance at 260 nm increases. This is because heating releases the hydrogen bond between both strands in the double-stranded DNA to dissociate it into single-stranded DNA (i.e. DNA melting). When all double-stranded DNAs are dissociated into single-stranded DNAs, the absorbance thereof indicates approximately 1.5 times the absorbance (i.e. absorbance of double-stranded DNAs only) obtained at the start of heating, whereby it may be determined that the melting is completed. On the basis of this phenomenon, the melting temperature (Tm) generally is defined as a temperature at which the absorbance has reached 50% of the total increase in absorbance.

The theoretical value of the Tm value may be calculated, for example, by using software "MELTCALC" (meltcalc. com/) under the setting conditions "Oligoconc [µM] 0.2, Na eq. [mM] 50". Also, the theoretical value of the Tm value may be determined by the nearest neighbor method, for example.

In the case of the melting curve analysis, the analysis method of the present invention may be configured so that the detection step includes, for example, the following steps (D1) and (D2), and the detection step detects an ALK fusion gene in the test sample by detecting the formation of a hybrid. (D1) the step of, while changing the temperature of a reaction system including an amplification product obtained in the amplification step and the probe, measuring a signal value that shows (i.e. is indicative of) a molten (i.e. unhybridized or dissociated) state of a hybrid between the amplification product and the probe
(D2) the step of detecting the formation of the hybrid between the amplification product and the probe on the basis of the change in the signal value accompanying the change in the temperature In the step (D1), for example, a double-stranded nucleic acid amplification product (for example, double-stranded DNA) obtained in the amplification step is dissociated into single-stranded nucleic acids (for example, single-stranded DNAs), and the single-stranded nucleic acid obtained by the dissociation is hybridized with the probe. This may be carried out by changing the temperature of the reaction system in the presence of the probe, for example. In this case, as described above, it is preferable that an amplification reaction is performed in the reaction system to which the probe is added beforehand, and thereafter, the temperature of the reaction system is changed.

The dissociation of a double-stranded nucleic acid into single-stranded nucleic acids may be performed by heat treatment. The heating temperature is, for example, a temperature that allows a double-stranded nucleic acid to be dissociated into single-stranded nucleic acids. The heating temperature is not particularly limited and is, for example, from 85° C. to 95° C. The heating time is not particularly limited and generally is from 1 second to 10 minutes, or from 1 second to 5 minutes.

The single-stranded nucleic acid obtained by the dissociation may be hybridized with the probe, for example, by decreasing the heating temperature employed in the dissociation step after the dissociation step. The temperature condition is, for example, from 40° C. to 50° C. The treatment time at the decreased temperature is not particularly limited, and is, for example, from 1 to 600 seconds.

Then, while changing the temperature of the reaction system in which the single-stranded nucleic acid had been hybridized with the probe, a signal value that indicates the molten state of the hybrid between the amplification product and the probe is measured. Specifically, for example, the reaction system is heated, i.e., the hybrid between the single-stranded nucleic acid and the probe is heated, and the change in signal value accompanying the temperature rise is measured. As described above, for example, when the probe is a fluorescence quenching probe in which cytosine (c) at the end is labeled, fluorescence of the probe decreases (or quenches) in the state where the probe is hybridized with the single-stranded nucleic acid, whereas the probe emits fluorescence in the state where the probe is dissociated from the single-stranded nucleic acid. Therefore, the hybrid with reduced (quenched) fluorescence may be heated gradually, and increase in fluorescence intensity accompanying the temperature rise may be measured, for example.

The temperature range in which the change in fluorescence intensity is to be measured is not particularly limited. The start temperature is, for example, from room temperature to 85° C., or from 25° C. to 70° C., and the end temperature is, for example, from 40° C. to 105° C. Furthermore, the rate of temperature rise is not particularly limited and is, for example, from 0.1° C./sec to 20° C./sec, or from 0.3° C./sec to 5° C./sec.

As described above, the step (D1) of the detection step is the step of measuring a signal value that indicates the molten state of a hybrid between the amplification product and the probe. The measurement of the signal may be the measurement of the absorbance at 260 nm as described above, or may be the measurement of the signal of the labeling substance. Specifically, a labeled probe labeled with a labeling substance may be used as the probe to perform the measurement of the signal of the labeling substance. The labeled probe may be, for example, a labeled probe that exhibits a signal when it is alone and does not exhibit a signal when it forms a hybrid, or a labeled probe that does not exhibit a signal when it is alone and exhibits a signal when it forms a hybrid. The former probe exhibits a signal when the probe is dissociated from the amplification product by heating, and the signal is reduced (or quenched) when the probe forms a hybrid (for example, double-stranded DNA) with the amplification product. On the other hand, the latter probe exhibits a signal when the probe forms a hybrid (for example, double-stranded DNA) with the amplification product, and the signal is reduced (or quenched) when the probe is dissociated from the amplification product by heating. Thus, by detecting the signal of the labeling substance, detection of the progress of melting of the hybrid, determination of the Tm value, and the like may be achieved, as in the case where the absorbance at 260 nm is measured, for example.

The signal of the labeling substance may be detected under a condition specific to the signal of the labeling substance, for example. Examples of the detection condition include an excitation wavelength and a detection wavelength. Examples of the labeled probe and the labeling substance include those described above.

As described above, the step (D2) of the detection step is the step of detecting the formation of the hybrid between the amplification product and the probe on the basis of the change in the signal value accompanying a change in the temperature measured in the step (D1). The detection of the formation of the hybrid on the basis of the change in the signal value may be performed by a common method. As a specific example, when the change in the signal value is observed, for example, it may be determined that the hybrid is formed. On the other hand, when there is no change in the signal value, for example, it may be determined that the hybrid is not formed. On the basis of this result, when the hybrid is not formed, it may be determined that there is no amplification product of a target variant, i.e., there is no amplification of the variant, which means that the variant is not present in the test sample. On the other hand, when the hybrid is formed, it may be determined that there is an amplification product of a target variant, i.e., there is amplification of the variant, which means that the variant is present in the test sample.

In the step (D2), for example, the Tm value is determined by analyzing the change in the signal. Specifically, the amount of change in fluorescence intensity (−d fluorescence intensity change/dt or d fluorescence intensity change/dt) per unit time at each temperature is calculated on the basis of the fluorescence intensity obtained. The temperature at which the amount of change is the greatest may be determined as the Tm value. In the case where the labeled probe used is the fluorescence quenching probe, for example, the amount of increase of the fluorescence intensity is measured, and the temperature at which the amount of increase of the fluorescence intensity (−d fluorescence intensity increase/dt) per unit time is the lowest or the temperature at which the amount of increase of the fluorescence intensity (d fluorescence intensity increase/dt) per unit time is the highest may be determined as the Tm value. On the other hand, when the probe used is not the fluorescence quenching probe but a probe that does not exhibit a signal when it is alone and exhibits a signal when it forms a hybrid, the amount of decrease in fluorescence intensity may be measured, as opposed to the above case.

Next, the latter method using an intercalator is a method in which an intercalator to be intercalated between base pairs of a double-stranded nucleic acid is used, for example. According to this method, for example, the amplification product may be detected based on the presence or absence of the intercalator intercalated into the amplification product or the amount of the intercalator intercalated into the amplification product.

The intercalator is not particularly limited, and a common intercalator such as SYBR (trademark) Green may be used, for example.

In the case where the intercalator is used, the analysis method of the present invention may be configured so that the detection step includes, for example, the following steps (D3) and (D4), and the detection step detects an ALK fusion gene in the test sample by detecting the intercalator intercalated into a double-stranded nucleic acid.

(D3) the step of measuring, with respect to a reaction system including an amplification product obtained in the amplification step and an intercalator, a signal value of the intercalator that shows a state where the intercalator is intercalated into a double-stranded nucleic acid (D4) the step of detecting the intercalator intercalated into the amplification product on the basis of the signal value In the analysis method of the present invention, for example, the amplification step using the primer reagent (or amplification reagent kit) of the present invention and the detection step using the intercalator may be performed in separate reaction systems, respectively, or may be performed in the same reaction system. In the former case, for example, the amplification reaction may be performed in a reaction system including the primer reagent, and thereafter, using the amplification product obtained in the reaction system of the amplification reaction and the intercalator, a reaction system for the detection step may be newly prepared. Also, in the former case, the amplification reaction may be performed in a reaction system including the primer reagent, and the intercalator further may be added to the reaction system of the amplification reaction during or after the amplification reaction to perform the detection step. In the latter case, the amplification reaction may be performed in a reaction system including the primer reagent and the intercalator, and the detection step may be performed in the reaction system as it is. According to the latter method, for example, there is no need to expose the reaction system to an external environment during or after the amplification reaction in order to add the intercalator, and the amplification reaction and the detection step may be performed continuously. In the case where the amplification step is performed by PCR, the latter method also is referred to as real-time PCR, for example.

In the reaction system of the detection step, the amount of the intercalator is not particularly limited.

The signal of the intercalator may be detected under a condition specific to the signal of the intercalator, for example. Examples of the detection condition include an excitation wavelength and a detection wavelength.

(5) Analysis Reagent Kit

As described above, the analysis kit according to the preset invention is an analysis reagent kit for an ALK fusion gene, including: the primer reagent according to the present invention. The amplification reagent kit of present invention is characterized in that it includes the primer reagent of the present invention, and other configurations and conditions are not particularly limited. According to the amplification reagent kit of the present invention, the plurality of variants of the ALK fusion gene may be amplified at the same time in the same reaction system, whereby the ALK fusion gene may be analyzed, detected, and quantified, for example. The descriptions regarding the primer reagent, the amplification reagent kit, the amplification method, and the analysis method of the present invention may be applied to an analysis reagent kit of the present invention, unless otherwise noted.

The analysis reagent kit of the present invention further may include a probe that hybridizes to an amplification product produced using the primer reagent, for example. The probe is not particularly limited, and examples thereof include those described above. The analysis reagent kit may include the Pack 1 probe reagent and the Pack 1 primer reagent in combination, the Pack 2 probe reagent and the Pack 2 primer reagent in combination, the Pack 3 probe reagent and the Pack 3 primer reagent in combination, and/or the Pack 4 probe reagent and the Pack 4 primer reagent in combination.

In the case where the analysis reagent kit of the present invention includes the probe, for example, the primer reagent and the probe reagent of the aforementioned combination may be contained in the same reaction system when they are in use.

When the analysis reagent kit of the present invention includes the Pack 1 primer reagent and at least one of the other Pack reagents, for example, the combination of the Pack 1 primer reagent and the Pack 1 probe reagent and the combination of the other Pack primer reagent(s) and the corresponding Pack probe reagent(s) may all be contained in the same reaction system when they are in use.

The analysis reagent kit of the present invention also may be configured so that, for example, with regard to each type of the Pack probe reagent, the combination of the Pack primer reagent and the Pack probe reagent are contained in the same reaction system when they are in use. In other words, for example, the combination of the Pack 1 primer reagent and the Pack 1 probe reagent and the combination of the other Pack primer reagent(s) and the corresponding Pack probe reagent(s) may form different reagent systems, respectively. In this case, the amplification step and the detection step may be performed separately with respect to the different reaction systems prepared by using the respective combinations of Pack primer reagents and corresponding Pack probe reagents.

In the present invention, hereinafter, a reagent including the Pack 1 primer reagent and the Pack 1 probe reagent is referred to as a "Pack 1 analysis reagent", a reagent including the Pack 2 primer reagent and the Pack 2 probe reagent is referred to as a "Pack 2 analysis reagent", a reagent including the Pack 3 primer reagent and the Pack 3 probe reagent is referred to as a "Pack 3 analysis reagent", and a reagent including the Pack 4 primer reagent and the Pack 4 probe reagent is referred to as a "Pack 4 analysis reagent", for example. Examples of the combination of the analysis reagents in the present invention include the combinations 1 to 8 shown below.

1. Pack 1 analysis reagent
2. Pack 1 analysis reagent/Pack 2 analysis reagent
3. Pack 1 analysis reagent/Pack 3 analysis reagent
4. Pack 1 analysis reagent/Pack 4 analysis reagent
5. Pack 1 analysis reagent/Pack 2 analysis reagent/Pack 3 analysis reagent
6. Pack 1 analysis reagent/Pack 2 analysis reagent/Pack 4 analysis reagent
7. Pack 1 analysis reagent/Pack 3 analysis reagent/Pack 4 analysis reagent
8. Pack 1 analysis reagent/Pack 2 analysis reagent/Pack 3 analysis reagent/Pack 4 analysis reagent (6) Drug Efficacy Determination Method As described above, the drug efficacy determination method according to the present invention is a test method for testing efficacy of a drug, including the steps of: analyzing an ALK fusion gene by the ALK fusion gene analysis method according to the present invention; and testing sensitivity to the drug on the basis of the presence or absence of the ALK fusion gene. The sensitivity to the drug allows a determination of the efficacy of the drug. The drug efficacy determination method of the present invention may be characterized in that it analyzes, detects, and/or quantifies an ALK fusion gene by the analysis method according to the present invention, and other conditions, steps, etc. are not particularly limited. The descriptions regarding the primer reagent, the amplification method, and the analysis method of the present invention may be applied to a drug efficacy determination method of the present invention, unless otherwise noted.

According to the drug efficacy determination method of the present invention, by utilizing an amplification reaction using the primer reagent (or amplification reagent kit) of the present invention, an ALK fusion gene may be analyzed, detected, and/or quantified easily with high sensitivity, and the drug efficacy may also be determined based on the analysis result. The dose of a drug may be reduced or increased, or the drug may be changed to another therapeutic drug depending on the determination of the drug efficacy, for example. Therefore, the drug efficacy determination method of the present invention is useful for determining the treatment plan of a disease, for example. Examples of a drug to be subjected to the drug efficacy determination include anticancer agents including an ALK inhibitor as an active ingredient. The anticancer agent may be, for example, an anticancer agent for lung cancer treatment, and specific examples thereof include crizotinib.

(7) Method for Testing the Possibility of Lung Cancer

The present invention also provides a method for testing the possibility of lung cancer, including the steps of: analyzing an ALK fusion gene in a biological sample obtained from a subject by the ALK fusion gene analysis method according to the present invention; and testing the possibility of lung cancer on the basis of the presence or absence of the ALK fusion gene. The test method according to the present invention is characterized in that it analyzes the ALK fusion gene by the analysis method of the present invention, and other conditions, steps, etc. are not particularly limited. The descriptions regarding the primer reagent of the present invention, the amplification method of the present invention, the analysis method of the present invention, and the like may be applied to the test method according to the present invention, unless otherwise stated.

According to the test method of the present invention, by utilizing an amplification reaction using the primer reagent of the present invention, an ALK fusion gene can be analyzed easily with high sensitivity, and the possibility of lung cancer can be tested on the basis of the analysis result.

The subject may be a human, for example. The above description regarding a biological sample also may be applied to the biological sample used in this test method, for example.

In the test method according to the present invention, the method for evaluating the possibility of lung cancer is not particularly limited. For example, when the biological sample obtained from the subject contains the ALK fusion gene, it can be evaluated that the subject has a risk or a high risk of developing lung cancer. On the other hand, when the biological sample obtained from the subject does not contain the ALK fusion gene, it can be evaluated that the subject has no risk or a low risk of developing lung cancer.

(8) Others

With respect to the primer reagent, the amplification reagent kit, the amplification method, the analysis method, the analysis reagent kit, and the drug efficacy determination method of the present invention, embodiments in which the Pack 1 primer reagent is an essential component have been described. However, for example, embodiments of the present invention may be those in which, instead of the Pack 1 primer reagent, one of the Pack 2 primer reagent, the Pack 3 primer reagent, and the Pack 4 primer reagent is used or two or more of them are used in combination.

It should be interpreted that the analysis method, the analysis reagent kit, and the drug efficacy determination method according to the present invention are not limited by the types of the primers or the amplification step using the primers, and they may be characterized by the use of the aforementioned probe(s), for example.

In this case, the analysis method of the present invention is characterized in that it includes the step of amplifying a template nucleic acid in a test sample and the step of detecting an ALK fusion gene in the test sample by detecting amplification of the template nucleic acid using a probe. The above descriptions may be applied to the analysis method of the present invention, unless otherwise noted. Also the above descriptions regarding the drug efficacy determination method may be applied to the drug efficacy determination method of the present invention except that an ALK fusion gene is analyzed, detected, and/or quantified by this analysis method of the present invention.

The primer to be used in the amplification step is not particularly limited, and the aforementioned primer reagents of the present invention may be used, for example. As the probe, the aforementioned probe reagents may be used according to the type of a target ALK fusion gene variant.

Also, the analysis reagent kit of the present invention is characterized in that it includes at least one of the aforementioned probe reagents, for example. The probe reagent is, for example, at least one selected from the group consisting of the Pack 1 probe reagent, the Pack 2 probe reagent, the Pack 3 probe reagent, and the Pack 4 probe reagent. One of them may be used alone or two or more of them may be used in combination. The analysis reagent kit further may include the aforementioned Pack primer reagent(s) according to the type of the probe reagent(s), for example.

Next, examples of the present invention will be described. The present invention is not limited by the following examples.

EXAMPLES

Example A1

In the present example, ALK fusion genes were amplified using the Pack 1 primer reagent to examine whether the respective variants may be amplified. Whether or not the amplification occurred was checked by Tm analysis using the Pack 1 probe.

(1) Samples

With the following oligonucleotides having the same sequences as the ALK fusion gene variants V1, V2, V3a, V3b, and V6 as templates, respective RNAs were synthesized. The RNAs were each mixed with RNase Free Water to prepare samples. The RNA concentration in each sample was 8000 copies/test.

```
V1 oligonucleotide
                                                              (SEQ ID NO: 32)
gggaaatatgaaaagccaaaatttgtgcagtgtttagcattcttggggaatggagatgttatactggagactc aggtggagtcatgcttatatggagcaaaactactgtagagcccacacctgggaaaggacctaaagtgtaccgc cggaagcaccaggagctgcaagccatgcagatggagctgcagagccctgagtacaagctgagcaagctccgca cctcgaccatcatgaccgactacaaccccaactactgattgctggcaagacctcctccatcagtgacctgaag gaggtgccgcggaaaaacatcaccctcattcggggtctgggccatggagcctttggggaggtgtatgaaggcc aggtgtccggaatgcccaacgacccaagccccagcaagtggctgtgaagacgctgcctgaagtGtgctctgaa caggacgaactggatttcctcatggaagccctgatcatcagcaaattcaaccaccagaacattgttcgctgca ttggggtgagcctgcaatccctgccc V2 oligonucleotide
                                                              (SEQ ID NO: 33)
gggaaatatgaaaagccaaaatttgtgcagtgtttagcattatggggaatggagatgttcttactggagactc aggtggagtcatgcttatatggagcaaaactactgtagagcccacacctgggaaaggacctaaaggtgtatat caaatcagcaaacaaatcaaagctcatgatggcagtgtgttcacactttgtcagatgagaaatgggatgttat taactggaggagggaaagacagaaaaataattctgtgggatcatgatctgaatcctgaaagagaaatagaggt tcctgatcagtatggcacaatcagagctgtagcagaaggaaaggcagatcaatttttagtaggcacatcacga aactttattttacgaggaacatttaatgatggcttccaaatagaagtacagggtcatacagatgagattgggg tcttgccacacatcccttcaaagatttgctcttgacatgtgctcaggacaggcaggtgtgcctgtggaactca atggaacacaggctggaatggaccaggctggtagatgaaccaggacactgtgcagattttcatccaagtggca cagtggtggccataggaacgcactcaggcaggtggtttgttctggatgcagaaaccagagatctagtttctat ccacacagacgggaatgaacagctctctgtgatgcgctactcaatagatggtaccttcctggctgtaggatct catgacaactttatttacctctatgtagtctctgaaaatggaagaaaatatagcagatatggaaggtgcactg gacattccagctacatcacacaccttgactggtccccagacaacaagtatataatgtctaactcgggagacta tgaaatattgtacttgtaccgccggaagcaccaggagctgcaagccatgcagatggagctgcagagccctgag tacaagctgagcaagctccgcacctcgaccatcatgaccgactacaaccccaactactgctttgctggcaaga cctcctccatcagtgacctgaaggaggtgccgcggaaaaacatcaccctcattcggggtctgggccatggagc ctttggggaggtgtatgaaggccaggtgtccggaatgcccaacgacccaagcccctgcaagtggctgtgaag acgctgcctgaagtGtgctctgaacaggacgaactggatttcctcatggaagccctgatcatcagcaaattca accaccagaacattgtt V3a oligonucleotide
                                                              (SEQ ID NO: 34)
tgatgttcaagatcgcctgtcagctcttgagtcacgagttcagcaacaagaagatgaaatcactgtgctaaag gcggctttggctgatgttttgaggcgtcttgcaatctctgaagatcatgtggcctcagtgaaaaaatcagtct caagtaaaggccaaccaagccctcgagcagttattcccatgtcctgtataaccaatggaagtggtgcaaacag aaaaccaagtcataccagtgctgtctcaattgcaggaaaagaaactattcatctgctgctaaaagtggtacag aaaaaaagaaagaaaaaccacaaggacagagagaaaaaaagaggaatctcattctaatgatcaaagtccaca aattcgagcatcaccttctccccagccctcttcacaaccctctccaaatacacagacaaactccagaaagcaag
```

-continued

```
aatgctactcccaccaaaagcataaaacgaccatcaccagctgaaaagtcacataattcttgggaaaattcag atgatagccgtaataaattgtcgaaaatacct tcaacacccaaattaataccaaaagttaccaaaactgcaga caagcataaagatgtcatcatcaaccaagtgtaccgccggaagcaccaggagctgcaagccatgcagatggag ctgcagagccctgagtacaagctgagcaagctccgcacctcgaccatcatgaccgactacaaccccaactact gattgctggcaagacctcctccatcagtgacctgaaggaggtgccgcggaaaaacatcaccctcattcggggt ctgggccatggagcctttggggaggtgtatgaaggccaggtgtccggaatgcccaacgacccaagcccctgc aagtggctgtgaagacgctgcctgaagtGtgctctgaacaggacgaactggatttcctcatggaagccctgat catcagcaa
```

V3b oligonucleotide
(SEQ ID NO: 35)
```
tgatgttcaagatcgcctgtcagctcttgagtcacgagttcagcaacaagaagatgaaatcactgtgctaaag gcggctttggctgatgttttgaggcgtcttgcaatctctgaagatcatgtggcctcagtgaaaaaatcagtct caagtaaaggccaaccaagccctcgagcagttattcccatgtcctgtataaccaatggaagtggtgcaaacag aaaaccaagtcataccagtgctgtctcaattgcaggaaaagaaactattcatctgctgctaaaagtggtacag aaaaaagaaagaaaaaccacaaggacagagagaaaaaaaagaggaatctcattctaatgatcaaagtccaca aattcgagcatcaccttctccccagccctcttcacaacctctccaaatacacagacaaactccagaaagcaag aatgctactcccaccaaaagcataaaacgaccatcaccagctgaaaagtcacataattcttgggaaaattcag atgatagccgtaataaattgtcgaaaatact tcaacacccaaattaataccaaaagttaccaaaactgcaga caagcataaagatgtcatcatcaaccaagcaaaaatgtcaactcgcgaaaaaaacagccaagtgtaccgccgg aagcaccaggagctgcaagccatgcagatggagctgcagagccctgagtacaagctgagcaagctccgcacct cgaccatcatgaccgactacaaccccaactactgattgctggcaagacctcctccatcagtgacctgaaggag gtgccgcggaaaaacatcaccctcattcggggtctgggccatggagcctttggggaggtgtatgaaggccagg tgtccggaatgcccaacgacccaagcccctgcaagtggctgtgaagacgctgcctgaagtGtgctctgaaca ggacgaactggatttcctcatggaagccctgatcatcagcaaattcaac
```

V6 oligonucleotide
(SEQ ID NO: 36)
```
aatctcatattttcttctggacctggagcggcaattcactaacaagaaaacagggaattttgggaaatatga aaagccaaaatttgtgcagtgtttagcattcttggggaatggagatgttatactggagactcaggtggagtca tgatatggagcaaaactactgtagagcccacacctgggaaaggacctaaaggaagtggcctgtgtagtgct tcaagggccaggctgccaggccatgttgcagctgaccacccacctgcagtgtaccgccGgaagcaccaggagc tgcaagccatgcagatggagctgcagagccctgagtacaagctgagca
```

(2) Reagents

A mixed reagent 1 (hereinafter also referred to as "P-mix1") including the Pack 1 primer reagent and the Pack 1 probe reagent was prepared by mixing the respective F primers, R primers, and probes so that the resultant mixture had the following composition. In the following composition, a primer set of TBP-F2 and TBP-R2 is a control primer set for checking whether an amplification reaction is normal and a probe 5PB-TBP-F2 is a control probe for detecting amplification by the control primer set. In each probe, FL, TAMRA (trademark), and PB are labeling fluorescent dyes. FL is BODIPY (trademark) FL and PB is Pacific Blue (trademark). Furthermore, RT-mix was prepared by mixing components so that the resultant mixture had the following composition.

TABLE 4

| P-mix1 | | | | |
|---|---|---|---|---|
| Components | | | | μL |
| Primers | F_V1/6 | cctgggaaaggacctaaag | SEQ ID No. 1 | 0.125 |
| | F_V2 | gggagactatgaaatattgtacttg | SEQ ID No. 2 | 0.125 |
| | F_V3a | ataaagatgtcatcatcaaccaag | SEQ ID No. 3 | 0.125 |
| | F_V3b | gcgaaaaaaacagccaag | SEQ ID No. 4 | 0.125 |

TABLE 4-continued

P-mix1

| | Components | | | μL |
|---|---|---|---|---|
| | R_V/multi | gctccatctgcatggc | SEQ ID No. 5 | 0.75 |
| | R_V6 | tggcagcctggccc | SEQ ID No. 6 | 0.75 |
| Control primers | TBP-F2 | aacagcctgccaccttac | SEQ ID No. 29 | 0.125 |
| | TBP-R2 | agtcatggcaccctgagg | SEQ ID No. 30 | 0.75 |
| Probes | P1-1 | (FL)-caccaggagctgca | SEQ ID No. 22 | 0.05 |
| | P1-2 | (TAMRA)-cctgtgtagtgcttcaa | SEQ ID No. 23 | 0.05 |
| Control Probe | 5-PB-TBP-F2 | (PB)-ctcagggcttggcc | SEQ ID No. 31 | 0.05 |
| | KCl | | | 0.75 |
| | dH₂O | | | 5.225 |
| | Total | | | 9 |

TABLE 5

RT-mix

| Components | μL |
|---|---|
| 1 mol/L DTT | 0.1 |
| 200 U/μL RNase Inhibitor | 0.25 |
| 200 U/μL reverse transcriptase | 0.01 |
| 1 mol/L Tris-HCl (pH 8.6) | 0.02 |
| dH₂O | 0.62 |
| Total | 1 |

In Table 5, the RNase Inhibitor is RNase Inhibitor (Recombinant) commercially available from TOYOBO, and the reverse transcriptase is SuperScript (registered trademark) III commercially available from Invitrogen.

(3) RT-PCR and Tm Analysis

A reaction solution was prepared using the above-described respective reagents, a commercially available reagent kit (i-densy (trademark) Pack UNIVERSAL, ARKRAY, Inc.), the P-mix1, and the RT-mix, and RT-PCR was performed using a gene analyzer (i-densy (trademark)). Specifically, in accordance with instructions for use attached to the reagent kit, 36 μL of the reagent kit, 9 μL of the P-mix1, 1 μL of the RT-mix, and 4 μL of the sample were mixed using the gene analyzer, thus preparing the mixture of 50 μL in total automatically. Then, RT-PCR was started. The conditions for RT-PCR were as follows. After treatment at 55° C. for 900 seconds and at 95° C. for 120 seconds, one cycle of treatment at 95° C. for 1 second and at 58° C. for 30 seconds was repeated 50 cycles, followed by treatment at 95° C. for 1 second and at 40° C. for 60 seconds. Subsequently, the reaction solution was heated from 40° C. to 75° C. with the rate of temperature rise at 1° C./3 seconds and the change in fluorescence intensity over time was measured to perform Tm analysis. The measurement wavelength was from 515 to 555 nm for the detection of BODIPY (trademark) FL, from 585 to 700 nm for the detection of TAMRA, and from 450 to 700 nm for the detection of Pacific Blue (trademark).

The results thereof are shown in FIG. 1. FIG. 1 shows graphs of the Tm analysis that shows the change in fluorescence intensity accompanying the temperature rise. In FIG. 1, the vertical axes indicate the change in fluorescence intensity (hereinafter also referred to as "fluorescence change amount") at each temperature. The unit of the vertical axis is a differential value "-d fluorescence intensity increase/dt" and is indicated as "-dF/dt". In FIG. 1, the horizontal axes indicate the temperature (° C.) at the time of measurement. In the Tm analysis, in the case where an amplification product is produced, the fluorescence of the probe is quenched when a hybrid is formed between a probe and the amplification product and the probe exhibits fluorescence when a probe is heated and dissociated from the amplification product. In the graph that shows the change in fluorescence intensity (-dF/dt), because a mountain-shaped peak shows the dissociation of the probe from the hybrid, it may be determined that an amplification product is present.

As shown in FIG. 1, by using the Pack 1 primer reagent and the Pack 1 probe reagent, all of the V1 sample, the V2 sample, the V3a sample, the V3b sample, and the V6 sample showed peaks. From this, it was found that these variants may be amplified by the Pack 1 primer reagent and the amplification products may be detected by the Pack 1 probe.

Example A2

In the present example, ALK fusion genes were amplified using the Pack 2 primer reagent to examine whether the respective variants may be amplified. Whether or not the amplification occurred was checked by Tm analysis using the Pack 2 probe.

(1) Samples

With the following oligonucleotides having the same sequences as the ALK fusion gene variants V8a, V8b, V4, and V4' as templates, respective RNAs were synthesized. The RNAs were each mixed with RNase Free Water to prepare samples. The RNA concentration in each sample was 8000 copies/test.

V8a oligonucleotide (SEQ ID NO: 37)
acagatgagctttggggtcttgccacacatcccttcaaagatttgctcttgacatgtgctcaggacaggcaggt gtgcctgtggaactcaatggaacacaggctggaatggaccaggctggtagatgaaccaggacactgtgcagatt -continued

```
ttcatccaagtggcacagtggtggccataggaacgcactcaggcaggccatgttgcagctgaccacccacctgc agtgtaccgccggaagcaccaggagctgcaagccatgcagatggagctgcagagccctgagtacaagctgagca agctccgcacctcgaccatcatgaccgactacaaccccaactactg
```

V8b oligonucleotide
(SEQ ID NO: 38)
```
caggcaggtgtgcctgtggaactcaatggaacacaggctggaatggaccaggctggtagatgaaccaggacact gtgcagattttcatccaagtggcacagtggtggccataggaacgcactcaggcaggagacaaaaacatgaagtc aattttcccaaaattaaactcattaaaaaatgtggaatgctgccaggccatgttgcagctgaccacccacctgc agtgtaccgccggaagcaccaggagctgcaagccatgcagatggagctgcagagccctgagtacaagctgagca agctccgcacctcgaccatcatgaccgactacaaccccaactactg
```

V4 oligonucleotide
(SEQ ID NO: 39)
```
caaatcaaagctcatgatggcagtgtgttcacactttgtcagatgagaaatgggatgttattaactggaggagg gaaagacagaaaaataattctgtgggatcatgatctgaatCctgaaagagaaatagagatatgctggatgagcc ctgagtacaagctgagcaagctccgcacctcgaCcatcatgaccgactacaaccccaactactgctttgctggc aagacctcctccatcagtgacctgaaggaggtgccgcggaaaaacatcaccctcattcggggtctgggccatgg agcctttggggaggtgtatgaaggccaggtgtccggaatgcccaac
```

V4' oligonucleotide
(SEQ ID NO: 40)
```
gggaaatatgaaaagccaaaatttgtgcagtgtttagcattcttggggaatggagatgttatactggagactca ggtggagtcatgcttatatggagcaaaactactgtagagcccacacctgggaaaggacctaaaggtgtatatca aatcagcaaacaaatcaaagctcatgatggcagtgtgttcacactttgtcagatgagaaatgggatgttattaa ctggaggagggaaagacagaaaaataattctgtgggatcatgatctgaatcctgaaagagaaatagaggttcct gatcagtatggcacaatcagagctgtagcagaaggaaaggcagatcaattttttagtaggcaagctccgcacctc gaccatcatgaccgactacaaccccaactactgattgctggcaagacctcctccatcagtgacctgaaggaggt gccgcggaaaaacatcaccctcattcggggtctgggccatggagcctttggggaggtgtatgaaggccaggtgt ccggaatgcccaacgacccaagcccctgcaagtggctgtgaagacgctgcctgaagtGtgctctgaacaggac gaactggatttcctcatggaagccctgatcatcagcaaattcaaccaccagaacat
```

(2) Reagents

A mixed reagent 2 (hereinafter also referred to as "P-mix2") including the Pack 2 primer reagent and the Pack 2 probe reagent was prepared by mixing the respective F primers, R primers, and probes so that the resultant mixture had the following composition.

TABLE 6

| | | P-mix2 | | | |
|---|---|---|---|---|---|
| | | Components | | | μL |
| Primers | F_V4 | gagatatgctggatgagcc | SEQ ID No. 9 | | 0.125 |
| | F_V4' | gaaggaaaggcagatcaattttttag | SEQ ID No. 10 | | 0.125 |
| | F_V8a | ataggaacgcactcaggc | SEQ ID No. 7 | | 0.125 |
| | F_V8b | aaatgtggaatgctgccag | SEQ ID No. 8 | | 0.125 |
| | R_V8a/b | tgtagtcggtcatgatgg | SEQ ID No. 11 | | 0.75 |
| | R_V4/4' | tacactgcaggtgggtg | SEQ ID No. 12 | | 0.75 |
| Probes | P2-1 | agctccgcacctc-(FL) | SEQ ID No. 24 | | 0.05 |
| | P2-2 | (TAMRA)-ccatgttgcagctga | SEQ ID No. 25 | | 0.05 |
| | | KCl | | | 0.75 |
| | | dH$_2$O | | | 6.15 |
| | | Total | | | 9 |

(3) RT-PCR and Tm Analysis

RT-PCR and Tm analysis were performed in the same manner as in Example A1, except that the aforementioned samples were used and the P-mix2 was used instead of the P-mix1.

Figure 2:
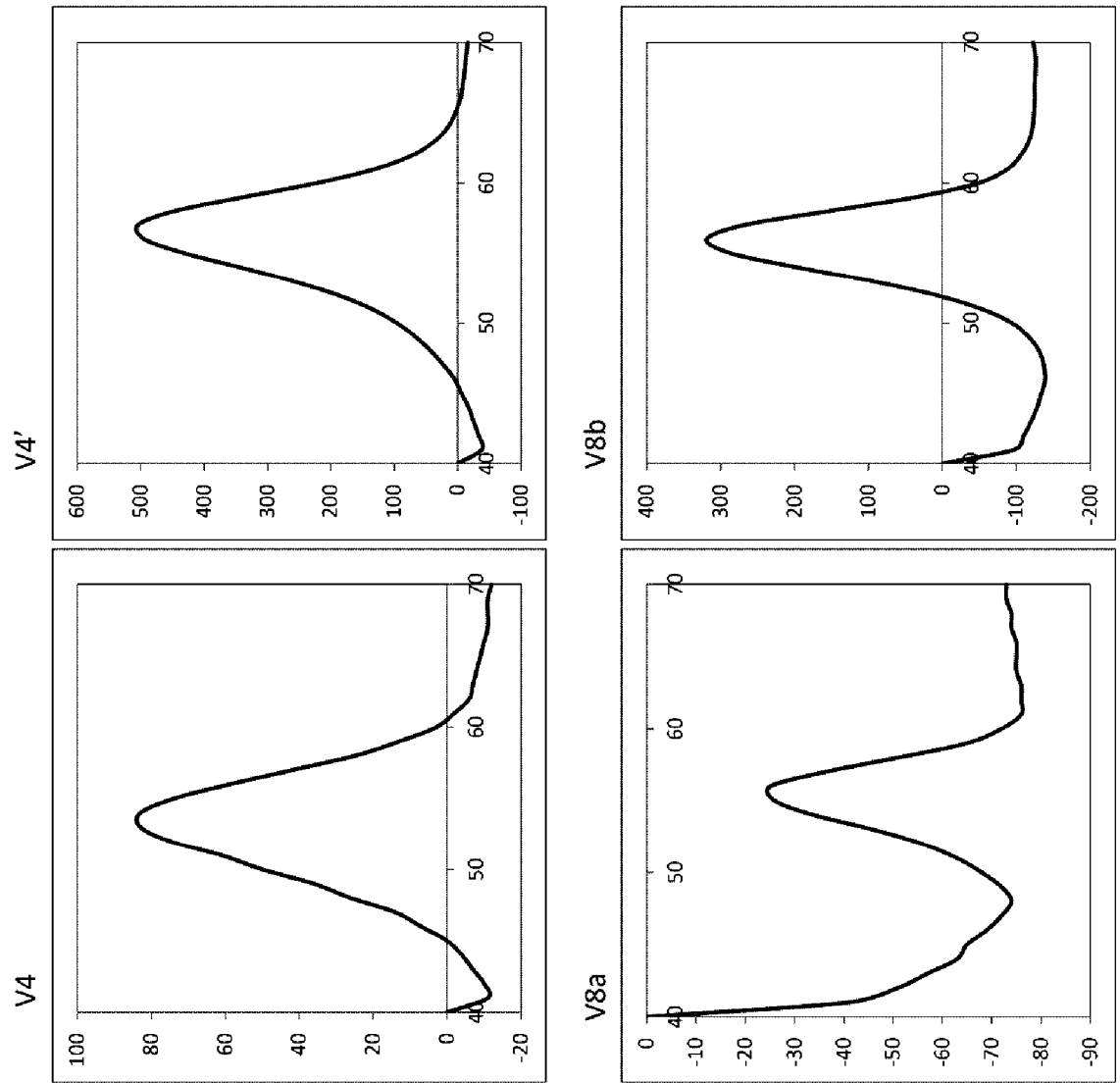
FIG. 2 shows graphs of Tm analysis results obtained in Example A2 of the present invention.

The results thereof are shown in FIG. 2. FIG. 2 shows graphs of the Tm analysis that shows the change in fluorescence intensity accompanying the temperature rise. In FIG. 2, the vertical axes and the horizontal axes are the same as those in FIG. 1 of Example A1.

As shown in FIG. 2, by using the Pack 2 primer reagent and the Pack 2 probe reagent, all of the V4 sample, the V4' sample, the V8a sample, and the V8b sample showed peaks. From this, it was found that these variants may be amplified by the Pack 2 primer reagent and the amplification products may be detected by the Pack 2 probe.

Example A3

In the present example, ALK fusion genes were amplified using the Pack 3 primer reagent to examine whether the respective variants may be amplified. Whether or not the amplification occurred was checked by Tm analysis using the Pack 3 probe.

(1) Samples

With the following oligonucleotides having the same sequences as the ALK fusion gene variants V5a, V5b, V7, and V9 as templates, respective RNAs were synthesized. The RNAs were each mixed with RNase Free Water to prepare samples. The RNA concentration in each sample was 8000 copies/test.

```
V5a oligonucleotide
                                                          (SEQ ID NO: 41)
ttctgctgcaagtacttctgatgttcaagatcgcctgtcagctcttgagtcacgagttcagcaacaagaagatga aatcactgtgctaaaggcggctttggctgatgttttgaggcgtcttgcaatctctgaagatcatgtggcctcagt gaaaaaatcagtctcaagtaaagtgtaccgccGgaagcaccaggagctgcaagccatgcagatggagctgcagag ccctgagtacaagctgagcaagctccgcacctcgaccatcatgaccgactacaaccccaactactgctttgctgg caagacctcctccatcagtgacctgaaggaggtgccgcggaa V5b oligonucleotide
                                                          (SEQ ID NO: 42)
atttctgctgcaagtacttctgatgttcaagatcgcctgtcagctcttgagtcacgagttcagcaacaagaagat gaaatcactgtgctaaaggcggctttggctgatgttttgaggcgtcttgcaatctctgaagatcatgtggcctca gtgaaaaaatcagtctcaagtaaaggttcagagctcaggggaggatatggagatccagggaggcttcctgtagga agtggcctgtgtagtgatcaagggccaggctgccaggccatgttgcagctgaccacccacctgcagtgtaccgcc ggaagcaccaggagctgcaagccatgcagatggagctgcagagccctgagtacaagctgagcaagctccgcacct cgaccatcatgaccgactacaaccccaactactgattgctggcaagacctcctccatcagtgacctgaaggaggt gccgcggaaaaacatcaccctcattcggggtctgggccatggagcctttggggaggtgtatgaaggccaggtgtc cggaatgcccaacgacccaagcccctgcaagtggctgtgaagacgctgcctgaagtGtgctctgaacaggacga actggatttcctcatggaagccctgatcatcagcaaattcaaccacca V7 oligonucleotide
                                                          (SEQ ID NO: 43)
agcaaaactactgtagagcccacacctgggaaaggacctaaaggtgtatatcaaatcagcaaacaaatcaaagct catgatggcagtgtgttcacactttgtcagatgagaaatgggatgttattaactggaggagggaaagacagaaaa ataattctgtgggatcatgatctgaatCctgaaagagaaatagagcaccaggagctgcaagccatgcagatggag ctgcagagccctgagtacaagctgagcaagctccgcacctcgaccatcatgaccgactacaaccccaactactgc tttgctggcaagacctcctccatcagtgacctgaaggaggtg V9 oligonucleotide
                                                          (SEQ ID NO: 44)
aaagccaaaatagtgcagtgatagcattcaggggaatggagatgacttactggagactcaggtggagtcatgata tatggagcaaaactactgtagagcccacacctgggaaaggacctaaaggtgtatatcaaatcagcaaacaaatca aagctcatgatggcagtgtgttcacactttgtcagatgagaaatgggatgttattaactggaggagggaaagaca gaaaaataattctgtgggatcatgatctgaatcctgaaagagaaatagaggacctgatcagtatggcacaatcag agctgtagcagaaggaaaggcagatcaattttagtaggcacatcacgaaactttaattacgaggaacatttaat gatggatccaaatagaagtacagggtcatacagatgagctaggggtcttgccacacatcccttcaaagatttgct cttgacatgtgctcaggacaggcaggtgtgcctgtggaactcaatggaacacaggctggaatggaccaggctggt
```

-continued

```
agatgaaccaggacactgtgcagattttcatccaagtggcacagtggtggccataggaacgcactcaggcaggtg gtttgttctggatgcagaaaccagagatctagtttctatccacacagacgggaatgaacagctctctgtgatgcg ctactcaatagtgtaccgccggaagcaccaggagctgcaagccatgcagatggagctgcagagccctgagtacaa gctgagcaagctccgcacctcgaccatcatgaccgactacaacccaactactgctagctggcaagacctcctcc atcagtgacctgaaggaggtgccgcggaaaaacatcaccctcattcggggtctgggccatggagcctaggggagg tgtatgaaggccaggtgtccggaatgcccaacgacccaagccctgcaagtggctgtgaagacgctgcctgaagt Gtgctctgaacaggacgaactggatacctcatggaagccctgatcatcagcaaattcaacca
```

(2) Reagents

A mixed reagent 3 (hereinafter, referred to as "P-mix3") including the Pack 3 primer reagent and the Pack 3 probe reagent was prepared by mixing the respective F primers, R primers, and probes so that the resultant mixture had the following composition. In the primer (F_V7), s is g or c, and the molar amount of the primer (F_V7) where s is g was the same as the molar amount of the primer (F_V7) where s is c.

TABLE 7

P-mix3

| | Components | | | μL |
|---|---|---|---|---|
| Primers | F_V5a/b | gtgaaaaaatcagtctcaagtaaag | SEQ ID No. 13 | 0.125 |
| | F_V7 | gatctgaatsctgaaagagaaatag | SEQ ID No. 14 | 0.125 |
| | F_V9 | tgtgatgcgctactcaatag | SEQ ID No. 15 | 0.125 |
| | R_V/multi | gctccatctgcatggc | SEQ ID No. 5 | 0.75 |
| | R_V5b | cctggatctccatatcctcc | SEQ ID No. 16 | 0.75 |
| Probes | P3-1 | (FL)-caccaggagctgca | SEQ ID No. 26 | 0.05 |
| | P3-2 | agtaaaggttcagagctc-(FL) | SEQ ID No. 27 | 0.05 |
| | KCl | | | 0.75 |
| | dH₂O | | | 6.275 |
| | Total | | | 9 |

(3) RT-PCR and Tm Analysis

RT-PCR and Tm analysis were performed in the same manner as in Example A1, except that the aforementioned samples were used and the P-mix3 was used instead of the P-mix1.

Figure 3:
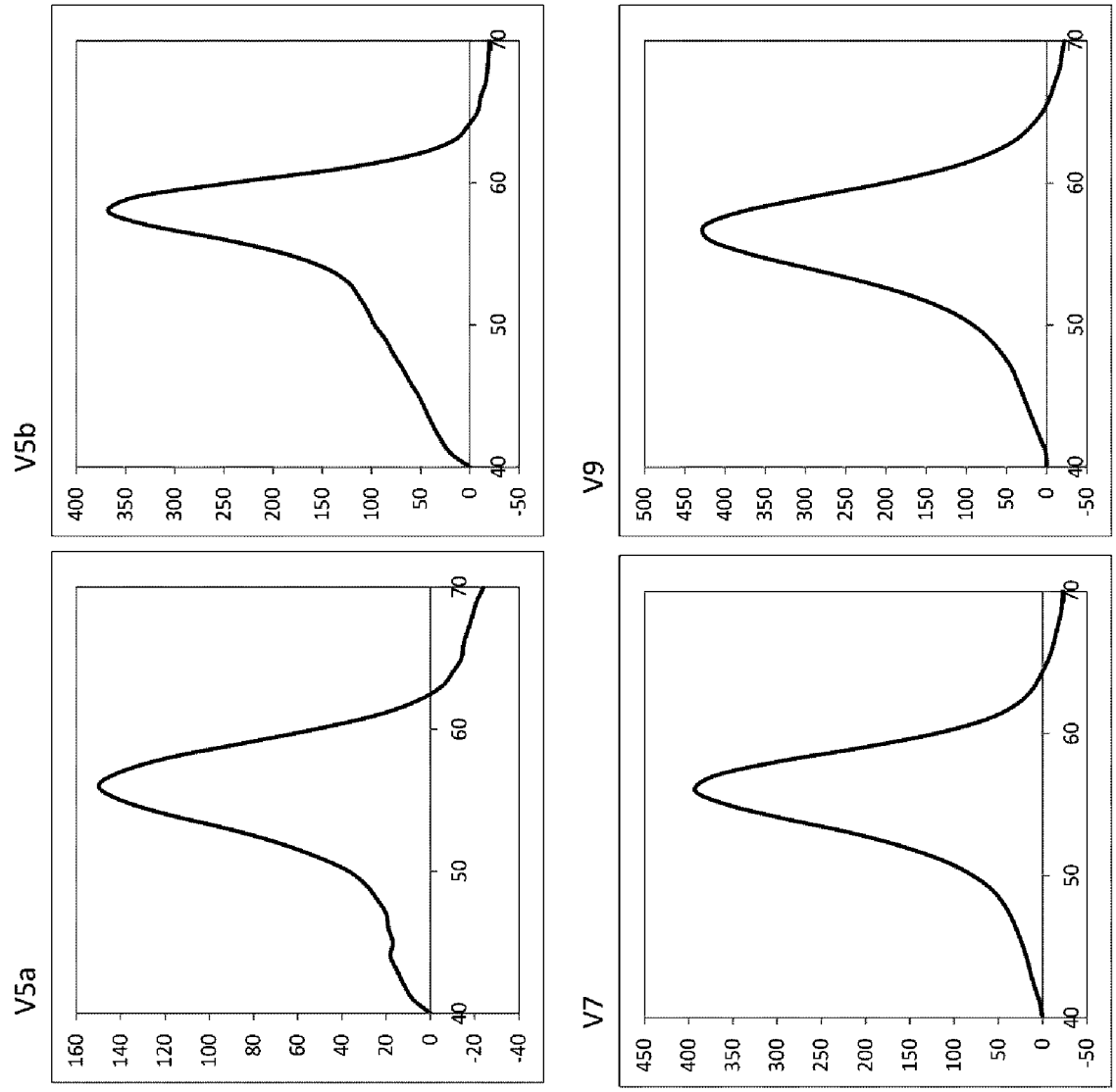
FIG. 3 shows graphs of Tm analysis results obtained in Example A3 of the present invention.

The results thereof are shown in FIG. 3. FIG. 3 shows graphs of the Tm analysis that shows the change in fluorescence intensity accompanying the temperature rise. In FIG. 3, the vertical axes and the horizontal axes are the same as those in FIG. 1 of Example A1.

As shown in FIG. 3, by using the Pack 3 primer reagent and the Pack 3 probe reagent, all of the samples showed peaks. From this, it was found that these variants may be amplified by the Pack 3 primer reagent and the amplification products may be detected by the Pack 3 probe.

Example A4

In the present example, ALK fusion genes were amplified using the Pack 4 primer reagent to examine whether the respective variants may be amplified. Whether or not the amplification occurred was checked by Tm analysis using the Pack 4 probe.

(1) Samples

With the following oligonucleotides having the same sequences as the ALK fusion gene variants KIF5B exon24-ALK, KIF5B exon15-ALK, KIF5B exon17-ALK, KLC1-ALK, and TFG-ALK as templates, respective RNAs were synthesized. The RNAs were each mixed with RNase Free Water to prepare samples. The RNA concentration in each sample was 8000 copies/test.

```
KIF5B exon24-ALK oligonucleotide
                                                        (SEQ ID NO: 45)
gcgacttcgagctacagctgagagagtgaaagattggaatcagcactgaaagaagctaaagaaaatgcatct cgtgatcgcaaacgctatcagcaagaagtagatcgcataaaggaagcagtcaggtcaaagaatatggccaga agagggcattctgcacagattgtgtaccgccggaagcaccaggagctgcaagccatgcagatggagctgcag agccctgagtacaagctgagcaagctccgcacctcgaccatcatgaccgactacaacccaactactgctttt gctggcaagacctcctccatcagtgacctgaaggaggtgccgcggaaaaacat
```

KIF5B exon15-ALK oligonucleotide
(SEQ ID NO: 46)
ccaaccaccagaaaaaacgagcagctgagatgatggcatctttactaaaagaccttgcagaaataggaattg ctgtgggaaataatgatgtaaagccaaccaccagaaaaaacgagcagctgagatgatggcatctttactaaa agaccttgcagaaataggaattgctgtgggaaataatgatgtaaagcaccaggagctgcaagccatgcagat ggagctgcagagccctgagtacaagctgagcaagctccgcacctcgaccatcatgaccgactacaacccccaa ctactgctttgctggcaagacctcctccatcagt KIF5B exon17-ALK oligonucleotide
(SEQ ID NO: 47)
caaaaaaatggaagaaaatgaaaaggagttagcagcatgtcagcttcgtatctctcaacatgaagccaaaat caagtcattgactgaataccttcaaaatgtggaacaaaagaaaagacagttggaggaatctgtcgatgccct cagtgaagaactagtccagcttcgagcacaagtgtaccgccggaagcaccaggagctgcaagccatgcagat ggagctgcagagccctgagtacaagctgagcaagctccgcacctcgaccatcatgaccgactacaacccccaa ctactgctttgctggcaagacctcctccatcagt KLC1-ALK oligonucleotide
(SEQ ID NO: 48)
aaccagggcaagtatgaagaagtagaatattattatcaaagagccctcgagatctaccagacaaaactggga cctgatgaccccaacgtggctaagacgaaaaataacctggcatcctgctatttgaaacaaggaaagttcaag caagcagaaacactgtacaaagagattctcactcgtgcacatgaaagggagtttggttctgtagatgtgtac cgccGgaagcaccaggagctgcaagccatgcagatggagctgcagagccctgagtacaagctgagcaagctc cgcacctcgaccatcatgaccgactacaacccccaactactgctttgctggcaag TFG-ALK oligonucleotide
(SEQ ID NO: 49)
tgaaactgacattatttgttaatggccagccaagacccatgaatcaagtcaggtgaaatatctccgtcgaga actgatagaacttcgaaataaagtgaatcgtttattggatagcttggaaccacctggagaaccaggaccttc caccaatattcctgaaaatgtgtaccgccggaagcaccaggagctgcaagccatgcagatggagctgcagag ccctgagtacaagctgagcaagctccgcacctcgaccatcatgaccgactacaacccccaactactgctttgc tggcaagacctcctccatcagtgacctgaaggaggtgccgcggaaaaacatca (2) Reagents A mixed reagent 4 (hereinafter also referred to as "P-mix4") including the Pack 4 primer reagent and the Pack 4 probe reagent was prepared by mixing the respective F primers, R primers, and probes so that the resultant mixture had the following composition.

TABLE 8

| | P-mix4 | | | |
|---|---|---|---|---|
| | Components | | | µL |
| Primers | F_KIF/e24 | ggcattctgcacagattg | SEQ ID No. 17 | 0.125 |
| | F_KIF/e15 | agaaataggaattgctgtggg | SEQ ID No. 18 | 0.125 |
| | F_KIFe17 | ccagcttcagagcacaag | SEQ ID No. 19 | 0.125 |
| | F_KLC1 | gggagtttggttctgtagatg | SEQ ID No. 20 | 0.125 |
| | F_TFG | ttccaccaatattcctgaaaatg | SEQ ID No. 21 | 0.125 |
| | R_V/multi | gctccatctgcatggc | SEQ ID No. 5 | 0.75 |
| Probe | P4-1 | (FL)-caccaggagctgca | SEQ ID No. 26 | 0.05 |
| | KCl | | | 0.75 |
| | dH$_2$O | | | 6.825 |
| | Total | | | 9 |

(3) RT-PCR and Tm Analysis

RT-PCR and Tm analysis were performed in the same manner as in Example A1 except that the aforementioned samples were used and the P-mix4 was used instead of the P-mix1.

Figure 4:
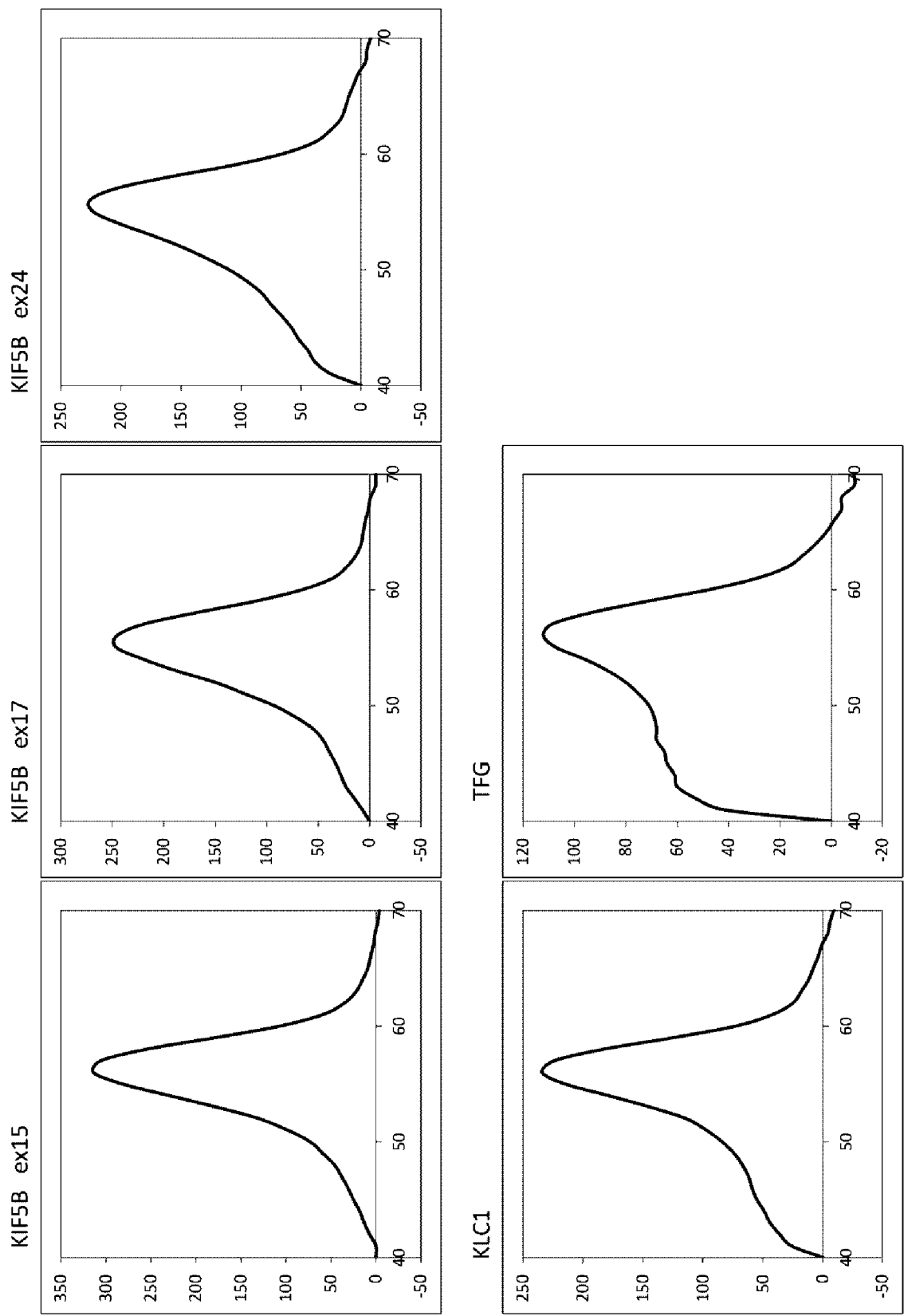
FIG. 4 shows graphs of Tm analysis results obtained in Example A4 of the present invention.

The results thereof are shown in FIG. 4. FIG. 4 shows graphs of the Tm analysis that shows the change in fluorescence intensity accompanying the temperature rise. In FIG. 4, the vertical axes and the horizontal axes are the same as those in FIG. 1 of Example A1.

As shown in FIG. 4, by using the Pack 4 primer reagent and the Pack 4 probe reagent, all of the samples showed peaks. From this, it was found that these variants may be amplified by the Pack 4 primer reagent and the amplification products may be detected by the Pack 4 probe.

While the present invention has been described above with reference to embodiments and examples, various changes that may become apparent to those skilled in the art may be made without departing from the scope of the present invention.

This application claims priority from Japanese Patent Application No. 2014-177356 filed on Sep. 1, 2014, and Japanese Patent Application No. 2015-165306 filed on Aug. 24, 2015. The entire disclosure of the Japanese Patent Application is incorporated herein by reference.

INDUSTRIAL APPLICABILITY

As specifically described above, according to the primer reagent of the present invention, variants V1, V2, V3a, V3b, and V6 of the ALK fusion gene may be amplified at the same time in the same reaction system. Thus, according to the present invention, two or more types of variants of the ALK fusion gene may be detected easily with the use of one reaction system. Therefore, the present invention is useful in diagnosis of the possibility of lung cancer and treatment of lung cancers, for example.

What is claimed is:

1. A detection reagent kit for detecting variants V1, V2, V3a, V3b and V6 simultaneously comprising:
   a forward primer consisting of the nucleotide sequence of SEQ ID NO: 1;
   a forward primer consisting of the nucleotide sequence of SEQ ID NO: 2;
   a forward primer consisting of the nucleotide sequence of SEQ ID NO: 3;
   a forward primer consisting of the nucleotide sequence of SEQ ID NO: 4;
   a reverse primer consisting of the nucleotide sequence of SEQ ID NO: 5;
   a reverse primer consisting of the nucleotide sequence of SEQ ID NO: 6; and
   a probe set comprising (i) a probe that is an oligonucleotide consisting of the nucleotide sequence of SEQ ID NO: 22 and that comprises a fluorescent dye attached to the 5' end cytosine base of the oligonucleotide; and (ii) a probe that is an oligonucleotide consisting of the nucleotide sequence of SEQ ID NO: 23 and that comprises a fluorescent dye attached to the 5' end cytosine base of the oligonucleotide.

2. The detection reagent kit according to claim 1, further comprising:
   a forward primer consisting of the nucleotide sequence of SEQ ID NO: 7;
   a forward primer consisting of the nucleotide sequence of SEQ ID NO: 8;
   a forward primer consisting of the nucleotide sequence of SEQ ID NO: 9;
   a forward primer consisting of the nucleotide sequence of SEQ ID NO: 10;
   a reverse primer consisting of the nucleotide sequence of SEQ ID NO: 11;
   a reverse primer consisting of the nucleotide sequence of SEQ ID NO: 12;
   a probe that is an oligonucleotide consisting of the nucleotide sequence of SEQ ID NO: 24 and that comprises a fluorescent dye attached to the 3' end cytosine base of the oligonucleotide; and
   a probe that is an oligonucleotide consisting of the nucleotide sequence of SEQ ID NO: 25 and that comprises a fluorescent dye attached to the 5' end cytosine base of the oligonucleotide.

3. The detection reagent kit according to claim 1, further comprising:
   a forward primer consisting of the nucleotide sequence of SEQ ID NO: 13;
   a forward primer consisting of the nucleotide sequence of SEQ ID NO: 14;

a forward primer consisting of the nucleotide sequence of SEQ ID NO: 15;
a reverse primer consisting of the nucleotide sequence of SEQ ID NO: 5; and
a reverse primer consisting of the nucleotide sequence of SEQ ID NO: 16;
a probe that is an oligonucleotide consisting of the nucleotide sequence of SEQ ID NO: 26 and that comprises a fluorescent dye attached to the 5' end cytosine base of the oligonucleotide; and
a probe that is an oligonucleotide consisting of the nucleotide sequence of SEQ ID NO: 27 and that comprises a fluorescent dye attached to the 5' end cytosine base of the oligonucleotide.

4. The detection reagent kit according to claim 1, further comprising:
a forward primer consisting of the nucleotide sequence of SEQ ID NO: 17;
a forward primer consisting of the nucleotide sequence of SEQ ID NO: 18;
a forward primer consisting of the nucleotide sequence of SEQ ID NO: 19;
a forward primer consisting of the nucleotide sequence of SEQ ID NO: 20;
a forward primer consisting of the nucleotide sequence of SEQ ID NO: 21;
a reverse primer consisting of the nucleotide sequence of SEQ ID NO: 5; and
a probe that is an oligonucleotide consisting of the nucleotide sequence of SEQ ID NO: 28 and that comprises a fluorescent dye attached to the 5' end cytosine base of the oligonucleotide.

5. The detection reagent kit further comprising:
a polymerase,
deoxynucleoside triphosphates (dNTPs), and
a buffer solution.

6. The detection reagent kit according to claim 5, wherein the polymerase is a DNA polymerase.

7. The detection reagent kit according to claim 5, further comprising albumin.

8. The detection reagent kit according to claim 5, further comprising RNase inhibitor, a reverse transcriptase, and a reducing agent.

9. The detection reagent kit according to claim 2, further comprising:
a polymerase,
deoxynucleoside triphosphates (dNTPs), and
a buffer solution.

10. The detection reagent kit according to claim 9, wherein the polymerase is a DNA polymerase.

11. The detection reagent kit according to claim 9, further comprising albumin.

12. The detection reagent kit according to claim 9, further comprising RNase inhibitor, a reverse transcriptase, and a reducing agent.

* * * * *